US010593035B2

(12) United States Patent
Onal et al.

(10) Patent No.: US 10,593,035 B2
(45) Date of Patent: Mar. 17, 2020

(54) IMAGE-BASED AUTOMATED MEASUREMENT MODEL TO PREDICT PELVIC ORGAN PROLAPSE

(71) Applicants: Sinan Onal, Tampa, FL (US); Susana Karina Lai-Yuen, Tampa, FL (US); Alfredo Weitzenfeld, Tampa, FL (US); Stuart Richard Hart, Tampa, FL (US)

(72) Inventors: Sinan Onal, Tampa, FL (US); Susana Karina Lai-Yuen, Tampa, FL (US); Paul Bao, Tampa, FL (US); Alfredo Weitzenfeld, Tampa, FL (US); Stuart Richard Hart, Tampa, FL (US)

(73) Assignee: University of South Florida, Tampa, FL (US)

( * ) Notice: Subject to any disclaimer, the term of this patent is extended or adjusted under 35 U.S.C. 154(b) by 465 days.

(21) Appl. No.: 15/074,640

(22) Filed: Mar. 18, 2016

(65) Prior Publication Data
US 2016/0275678 A1    Sep. 22, 2016

Related U.S. Application Data

(60) Provisional application No. 62/134,702, filed on Mar. 18, 2015.

(51) Int. Cl.
*G06T 7/00* (2017.01)
*G06K 9/62* (2006.01)
(Continued)

(52) U.S. Cl.
CPC .......... *G06T 7/0012* (2013.01); *G06K 9/4642* (2013.01); *G06K 9/6256* (2013.01);
(Continued)

(58) Field of Classification Search
None
See application file for complete search history.

(56) References Cited

U.S. PATENT DOCUMENTS

2013/0030278 A1*  1/2013  Seong ............... G06T 7/0012
                                              600/407
2013/0064439 A1*  3/2013  Khurd ............... G06K 9/6226
                                              382/131

OTHER PUBLICATIONS

Woodfield et al. (Imaging Pelvic Floor Disorders: Trend Toward Comprehensive MRI; RJR:194, Jun. 2010).*

(Continued)

*Primary Examiner* — Bill Thomson
*Assistant Examiner* — Shahdeep Mohammed
(74) *Attorney, Agent, or Firm* — Smith & Hopen, P.A.; Steven M. Forte; Nilay J. Choksi

(57) ABSTRACT

A system and methodology for the automated localization, extraction, and analysis of MRI-based features with clinical information to improve the diagnosis of pelvic organ prolapse (POP). The system can automatically identify reference points for pelvic floor measurements on MRI rapidly and consistent. It provides a prediction model that analyzes the correlation between current and new MRI-based features with clinical information to differentiate patients with and without POP. This system will enable the high throughput analysis of MR images for their correlation with clinical information to better detect POP. The presented system can also be applied to the automated localization and extraction of MRI features for the diagnosis of other diseases where clinical examination is not adequate.

22 Claims, 21 Drawing Sheets

(51) Int. Cl.
  G06K 9/46 (2006.01)
  A61B 5/055 (2006.01)
(52) U.S. Cl.
  CPC ............ *G06K 9/6269* (2013.01); *A61B 5/055* (2013.01); *G06K 2209/051* (2013.01); *G06T 2207/10088* (2013.01); *G06T 2207/30004* (2013.01)

(56) References Cited

OTHER PUBLICATIONS

Fripp et al. ("Automatic segmentation of bone and extraction of the bone-cartilage interface from magnetic resonance image of the knee"; Phys. Med. Biol. 52 (2007).*
Over Onal et al. ("MRI-Based Segmentation of Pubic Bone for Evaluation of Pelvic Organ Prolapse"; IEE journal of biomedical and health informatics; pp. 1370-1378; Mar. 6, 2014).*
Cuingnet et al., Automatic Detection and Segmentation of Kidneys in 3D CT Images Using Random Forests. MICCAI: Part III. LNCS. 2012. vol. 7512: 66-74.
Onal et al., MRI based Segmentation of Pubic Bone for Evaluation of Pelvic Organ Prolapse. IEEE Journal of Biomedical and Health Informatics. 2014. vol. 18 (No. 4): 1370-1378.
Polat and Gunes. Breast cancer diagnosis using least square support vector machine. Digital Signal Processing. 2007. vol. 17: 694-701.
Akay. Support vector machines combined with feature selection for breast cancer. Expert Systems with Applications. 2009. vol. 36: 3240-3247.
Mouritsen and Larsen. Symptoms, bother and POPQ in women referred with pelvic organ prolapse. Int Urogynecol J. 2003. vol. 14: 122-127.
Goh et al., Dynamic MR imaging of the pelvic floor in asymptomatic subjects. AJR Am J Roentgenol. 2000. vol. 174: 661-666.
Healy et al., Dynamic MR imaging compared with evacuation proctography when evaluating anorectal configuration and pelvic floor movement. AJR Am J Roentgenol. 1997. vol. 169: 775-779.
Lienemann et al., Dynamic MR colpocystorectography assessing pelvic floor descent. Eur Radiol. 1997. vol. 7: 1309-17.
Onal et al., Assessment of a Semi-Automated Pelvic Floor Measurement Model for the Evaluation of Pelvic Organ Prolapse on MRI. International Urogynecology Journal. 2014. vol. 25: 767-773.
Ubeyli. Implementing automated diagnostic systems for breast cancer detection. Expert Systems with Applications. 2007. vol. 33: 1054-1062.
Lienemann et al., Assessment of pelvic organ descent by use of functional cine-MRI: which reference line should be used? Neurourol Urodyn. 2004. vol. 23: 33-37.
Gousse et al., Dynamic half Fourier acquisition, single shot turbo spin-echo magnetic resonance imaging for evaluating the female pelvis. J Urol. 2000. vol. 164: 1606-1613.
Kelvin et al., Female pelvic organ prolapse: diagnostic contribution of dynamic cystoproctography and comparison with physical examination. AJR Am J Roentgenol. 1999. vol. 173: 31-37.
Fauconnier et al., Dynamic magnetic resonance imaging for grading pelvic organ prolapse according to the international continence society classification: Which line should be used? . Neurourol Urodyn. 2007. vol. 27: 191-197.
Pannu et al., MRI Diagnosis of Pelvic Organ Prolapse Compared with Clinical Examination. Academic Radiology. 2011. vol. 18 (No. 10): 1245-51.
Cortes et al., Clinical Examination and Dynamic Magnetic Resonance Imaging in Vaginal Vault Prolapse. Obstetrics & Gynecology. 2004. vol. 103 (No. 1): 41-46.
Ismail et al., Unilateral coronal diameters of the levator hiatus: baseline data for the automated detection of avulsion of the levator ani muscle. Ultrasound Obstet Gynecol. 2010. vol. 36: 375-378.
Robinson et al., Prediction of pelvic organ prolapse using an artificial neural network. American Journal of Obstetrics and Gynecology. 2008. vol. 199: 193.e1-191.e6 (Aug. 2008).

Onal et al., Pubic Bone Segmentation for Diagnosis of Pelvic Organ Prolapse. 6th Annual College of Engineering Research Day, Nov. 6, Tampa, FL.
Onal et al., Combined Supervised and Unsupervised Segmentation of Pubic Bone for Diagnosis of Pelvic Organ Prolapse. Informs Annual Meeting. 2013. Minneapolis, MN: 1-10.
Li et al., Distance Regularized Level Set Evolution and Its Application to Image Segmentation. IEEE Transactions on Image Processing. 2010. vol. 19: 3243-3254.
Fayyad et al., How accurate is symptomatic and clinical evaluation of prolapse prior to surgical repair? Int Urogynecol J. 2007. vol. 18: 1179-1183.
Rohlfing et al., Evaluation of atlas selection strategies for atlas-based image segmentation with application to confocal microscopy images of bee brains. Neuroimage. 2004. vol. 21: 1428-1442.
Onal et al., Quantitative assessment of new MRI-based measurement to differentiate low and high stages of pelvic organ prolapse using support vector machines. Int Urogynecol J. 2015. vol. 26: 707-713.
Dallenbach et al., Incidence rate and risk factors for vaginal vault prolapse repair after hysterectomy. Int Urogynecol J. 2008. vol. 19: 1623-1629.
Bump et al., The Standardization of Terminology of Female Pelvic Organ Prolapse and Pelvic Floor Dysfunction. Am J Obstet Gynecol. 1996. vol. 175: 10-17.
Altman et al., Assessment of Posterior Vaginal Wall Prolapse: Comparison of Physical Findings to Cystodefecoperitoneography. Int Urogynecol J. 2005. vol. 16: 96-103.
Groenendijk et al., Correlation between posterior vaginal wall defects assessed by clinical examination and by defecography. Int. Urogynecol J. 2008. vol. 19: 1291-1297.
Colaiacomo et al., Dynamic MR imaging of the pelvic floor: a pictorial review. Radiographics. 2009. vol. 29 (No. 3): e35.
Onal et al., Image based measurements for evaluation of pelvic organ prolapse. Journal of Biomedical Science and Engineering. 2013. vol. 6: 45-55.
Broekhuis et al., A systematic review of clinical studies on dynamic magnetic resonance imaging of pelvic organ prolapse: the use of reference lines and anatomical landmarks. Int Urogynecol J. 2009. vol. 20: 721-729.
Lakeman et al., Dynamic magnetic resonance imaging to quantify pelvic organ prolapse: reliability of assessment and correlation with clinical findings and pelvic floor symptoms. Int. Urogynecol J. 2012. vol. 23: 1547-1554.
Tamez-Pena et al., Unsupervised statistical segmentation of multispectral volumetric MR images. Part of the SPIE Conference on Image Processing. 1999: 300-311.
Adams and Bischof. Seeded region growing. IEEE Trans. Pattern Anal. Machine Intell. 1994. vol. 16 (No. 6): 641-647.
Fripp et al., Automatic segmentation of the bone and extraction of the bone-cartilage interface from magnetic resonance images of the knee. Phys. Med. Biol. 2007. vol. 52: 1617-1631.
Brem et al., Magnetic resonance image segmentation using semi-automated software for quantification of knee articular cartilage—initial evaluation of a technique for paired scans. Skeletal Radiology. 2009. vol. 38: 505-511.
Chan and Vese. Active Contours Without Edges. IEEE Transaction on Image Processing. 2001.vol. 10 (No. 2): 266-277.
Folkesson et al., Segmenting articular cartilage automatically using a voxel classification approach. IEEE Transactions on Medical Imaging. 2007. vol. 26 (No. 1): 106-115.
Shim et al., Knee cartilage: Efficient and reproducible segmentation on highspatial-resolution MR images with the semiautomated graph-cut algorithm method. Radiology. 2009. vol. 251 (No. 2): 548-556.
Lorigo et al., Segmentation of Bone in Clinical Knee MRI Using Based Geodesic Active Contours. MICCAI: LCNS. 1998. vol. 1496: 1195-1205.
Schmid and Thalmann. MRI bone segmentation using deformable models and shape priors. MICCAI: Part 1: LNCS. 2008. vol. 5241: 119-126.
Carballido-Gamio. Normalized cuts in 3-D for spinal MRI segmentation. IEEE Trans. Med. Img., 2004. vol. 23 (No. 1): 36-44.

(56) References Cited

OTHER PUBLICATIONS

Liu et al., Interactive separation of segmented bones in ct volumes using graph cut. MICCAI: Part 1: LNCS. 2008. vol. 5241: 296-304.
Boykov and Kolmogorov. An experimental comparison of min-cut/max-flow algorithms for energy minimization in vision. IEEE Trans. Pattern Anal. Mach. Intell. 2004. vol. 26 (No. 9): 1124-1137.
Boykov. Interactive graph cuts for optimal boundary & region segmentation of objects in N-D images. Eighth IEEE International Conference on Computer Vision (ICCV 2001). 2001: 105-112.
Viola and Jones. Rapid object detection using a boosted cascade of simple features. Proc. IEEE Comput. Soc. Conf. Comput. Vis. Pattern Recog. 2001: I-511-I-518.
Bourgeat et al., MR image segmentation of the knee bone using phase information. Med. Image Anal. 2007. vol. 11: 325-335.
Van Ginneken et al., Segmentation of anatomical structures in chest radiographs using supervised methods: A comparative study on a public database. Medical Image Analysis. 2006. vol. 10: 19-40.
Onal et al., MRI-based Semi-Automatic Pelvimetry Measurement for Pelvic Organ Prolapse Diagnosis. 11th International Conference on Information Sciences, Signal Processing and Their Applications: Main Tracks (ISSPA 2012). 2012: 804-808.
Haralick and Shapiro. Survey: image segmentation techniques. Computer Vision Graphics Image Process. 1985. vol. 29: 100-132.
Pasquier et al., Automatic Segmentation of Pelvic Structures From Magnetic Resonance Images for Prostate Cancer Radiotherapy. International Journal of Radiation Oncology Biology Physics. 2007. vol. 68 (No. 2): 592-600.
Chen et al., Image segmentation via adaptive K-mean clustering and knowledge based morphological operations with biomedical applications. IEEE Transactions on Image Processing. 1998. vol. 7 (No. 12): 1673-1683.
Steinbach et al., A Comparison of Document Clustering Techniques. IEEE KDD workshop on text mining. 2000. vol. 400: 1-2.
Schmid et al., Evaluation of interest point detectors. International Journal of Computer Vision. 2000. vol. 37: 151-172.
Cui et al., A new automated method for the segmentation and characterization of breast masses on ultrasound images. Med. Phys. 2009. vol. 36 (No. 5): 1553-1565.
Maghsoodloo et al., Strengths and limitations of taguchi's contributions to quality, manufacturing, and process engineering. J. Manufacturing systems. 2004. vol. 23 (No. 2): 73-126.
Kurkure et al., Automated segmentation of thoracic aorta in non-contrast CT images. IEEE Intl. Symp. Biomedical Im. (ISBI 2008). 2008: 29-32.
Van Ginneken et al., Robust segmentation and anatomical labeling of the airway tree from thoracic CT scans. MICCAI: Part 1: LCNS. 2008. vol. 5241: 219-226.
Rahim et al., Automatic estimation of pelvic organ anatomical references. IEEE Eng Med Biol Soc. (EMBS). 2011: 5124-5127.
Fenchel et al., Automatic labeling of anatomical structures in MR fastview images using a statistical atlas. MICCAI: LCNS. 2008. vol. 5241: 576-584.
Speksnijder et al., Agreement and reliability of pelvic floor measurements during contraction using three-dimensional pelvic floor ultrasound and virtual reality. Ultrasound Obstet Gynecol. 2012. vol. 40: 87-92.
Han et al., Atlas-based auto-segmentation of head and neck CT images. MICCAI: Part II: LCNS. 2008. vol. 5242: 434-441.
Freiman et al., Classification of suspected liver metastases using fMRI images: A machine learning approach. MICCAI: Part 1: LCNS. 2008. vol. 5241: 93-100.
Prasad and Sowmya. Multi-level classification of emphysema in HRCT lung images using delegated classifiers. MICCAI: Part 1: LNCS. 2008. vol. 5241: 59-66.
Zheng et al., Four-chamber heart modeling and automatic segmentation for 3-D cardiac CT volumes using marginal space learning and steerable features. IEEE Transactions on Medical Imaging. 2008. vol. 27 (No. 11): 1668-1681.
Zheng et al., Marginal Space Learning for Efficient Detection of 2D/3D Anatomical Structures in Medical Images. IPMI: LCNS. 2009. vol. 5636: 411-422.
Zhou et al., A boosting regression approach to medical anatomy detection. IEEE Conference on Computer Vision and Pattern Recognition. 2007: 1-8.
Criminisi et al., Regression Forests for Efficient Anatomy Detection and Localization in CT Studies. LNCS. 2011. vol. 6533: 106-117.

\* cited by examiner

IMAGE-BASED AUTOMATED MEASUREMENT MODEL TO PREDICT PELVIC ORGAN PROLAPSE

CROSS-REFERENCE TO RELATED APPLICATIONS

This nonprovisional application claims priority to U.S. Provisional Application Ser. No. 62/134,702, entitled "Image-Based Automated Measurement Model to Predict Pelvic Organ Prolapse", filed Mar. 18, 2015 by the same inventors, the entirety of which is incorporated herein by reference.

BACKGROUND OF THE INVENTION

1. Field of the Invention

This invention relates, generally, to pelvic organ prolapse. More specifically, it relates to a methodology for analyzing medical images to facilitate prediction and/or diagnosis of pelvic organ prolapse.

2. Brief Description of the Prior Art

Pelvic organ prolapse (POP) is a serious health condition that affects about 30-50% of women in the U.S. [1] and has direct costs of approximately $1 billion/year. POP symptoms are generally nonspecific, and it occurs when a pelvic organ such as bladder, uterus, small bowel and rectum drops from its normal position and pushes against the vaginal walls. It can cause significant problems such as a vaginal bulge, bowel and bladder incontinence, and sexual dysfunction. Approximately 75% of women reported an effect on their quality of life due to POP [51].

The International Continence Society (ICS) recommends the use of the Pelvic Organ Prolapse Quantification (POP-Q) system [2] for diagnosis of POP through clinical examination. POP-Q is currently considered the gold standard for assessing POP. However, clinical examination has been found to be inadequate in about 41% of the cases. Groenendijk et al. [5] found that the diagnostic accuracy of clinical examination for POP was 0.42. Therefore, there is a major need to improve the diagnosis of POP.

Dynamic magnetic resonance imaging (MRI) of the pelvic floor has become increasingly popular in assessing POP cases that may not be evident during clinical examination (due to the inaccuracies of clinical examination). Dynamic MRI complements clinical examination by providing a global assessment of the movements and interactions of pelvic floor organs, while avoiding the use of ionizing radiation [6]. During the analysis of dynamic MRI, anatomical landmarks/reference points are manually identified on pelvic bone structures (pubic bone, sacral promontory, and coccyx) on the midsagittal plane to determine reference lines and measurements for grading and determining the stages of POP (see FIG. 1A) [7]. Dynamic MRI can be particularly useful in analyzing multiple compartment prolapse cases. However, the manual identification of these measurements is a time-consuming and subjective procedure. Based on these points, reference lines are drawn to measure and define the severity of POP as shown in FIG. 1B.

More specifically, the most commonly used reference lines for measuring POP are the pubococcygeal line (PCL), and the mid-pubic line (MPL). The PCL is determined by the inferior border of the pubic bone and the last visible coccygeal joint, while the MPL is a midsagittal long axis of the symphysis pubis and extends through the level of the vaginal hymen [52, 53]. Distances are then measured from PCL and MPL to the furthest most descent of the pelvic organs including the bladder neck, cervix, and anorectal junction on the images when the patient is at rest and under maximum pelvic strain. Based on these distances, the severity of prolapse can be graded as mild, moderate, or severe [54].

Although there are commonly used reference lines, as discussed, there is no standardized system for evaluating MRI measurements for POP, and previous studies that analyze the correlation between clinical and MRI measurements for POP diagnosis have been limited. Moreover, these studies used few features (variables) based on commonly used MRI reference lines such as PCL and MPL. Current studies have only analyzed small sample sizes resulting in limited and non-comparable data [8, 9]. This has restricted the correlation analysis of MRI measurements with clinical and surgical outcomes/information, as well as restricting the validation of newly proposed reference lines. A functional correlation between MRI measurements and POP has been found for two types of prolapse: anterior and apical. However, for the posterior type of prolapse, no correlation has been found, making this the most difficult type of prolapse to diagnose.

As noted, dynamic MRI is a promising complementary diagnostic tool for POP but appropriate validation has been limited. Automating the identification of reference points, lines, and measurements is expected to facilitate the high throughput analysis of images and improve the evaluation of POP. To this aim, pelvic bone structures need to be segmented and their corresponding reference points identified automatically. However, segmentation of bone structures on MRI is a challenging task since the pixel intensities of bones can be very similar to the pixel intensities of other structures such as soft tissue, fat and air. For this reason, challenges remain for bone segmentation on MRI; these challenges have not been overcome by the conventional art. Therefore, there is a major need to investigate the correlation between clinical and MRI-based features as well as to test new MRI-based features that can potentially improve the prediction of prolapse, particularly for posterior prolapse.

Previous methods for segmentation on MRI include region growing approaches [10, 11], active shape models [12], general deformable models [13-15], clustering methods [16], and graph-based approaches [17]. Lorigo et al. [18] segmented the knee bone using texture-based geodesic active contours. Fripp et al. [12] segmented the knee bone using 3D active shape models initialized by affine registration to an atlas. Shape models [19], normalized cuts [20] and graph cut [21-23] have been used to segment the femur and hip bones, spinal, and femoral head, respectively. Schmid et al. [19] presented a technique based on physically-based deformable models and prior shape knowledge to segment the femur and hip bones on MRI. Yin et al. [24] used graph cuts for knee-joint bone and cartilage segmentation.

Recently, segmentation techniques based on statistical classification have been used for bone segmentation on MRI [25, 26]. These techniques group pixels or voxels based on distinguished features such as intensities, gradients and texture. Simple intensity-based features do not provide successful segmentation results because different tissues have overlapping image intensity values. Bourgeat et al. [25] used Gabor filter features extracted from the phase of MR signal to improve texture discrimination in bone segmentation. van Ginneken et al. [26] combined texture based classification with the anatomically valid shape information of the chest structure to constrain the segmentation. Although these methods present promising results, the main drawbacks are high computation time, initialization sensitivity, definition of many parameters, and lack of leak detection processes.

Various approaches have been proposed for the automated localization of multiple organs such as heart, liver, spleen, lungs, kidneys and bladder on medical images using geometric methods, statistical atlas-based techniques, and supervised methods [35-42]. Among supervised methods, there has been an increasing interest in regression-based approaches for anatomical structure localization, since organs and tissues in the human body have known relative arrangement. Zheng et al. [43]proposed an approach called marginal space learning (MSL) that uses a set of classifiers based on probabilistic boosting tree (PBT) to predict the position, position orientation and full 3D pose. In [44], the authors further expanded this idea to non-rigid marginal space learning using statistical shape models. Zhou et al. [45] introduced an approach based on boosting ridge regression to detect and localize the left ventricle (LV) in cardiac ultrasound 2D images. Criminisi et al. [46]proposed regression forests to predict the location of multiple anatomical structures in CT scans. Cuingnet et al. [47] presented an improved regression forest by adding a refinement step to the detection process to find kidneys in CT scans. These methods use the difference in mean intensities to locate the bounding boxes of the anatomical structures on the images. However, considering only intensity levels is not sufficient for the localization of anatomical structures such as bones on MRI.

Further attempts have been made to overcome the foregoing drawbacks of the conventional art. Examples include [64]-[68]. However, each of the foregoing disclosures/technologies includes any one or more of the drawbacks previously discussed, and they may not be fully effective and/or not completely accurate.

One or more of the current inventors' previous publications include the following:

S. Onal, S. Lai-Yuen, P. Bao, A. Weltzenfeld, K. Greene, R. Kedar, S. Hart, "Assessment of a semiautomated pelvic floor measurement model for evaluating pelvic organ prolapse on MRI", Int Urogynecol J, 25(6):767-773 (published Jan. 16, 2014).

Onal, S., Lai-Yuen, S., Bao, P., Weitzenfeld, A., Stuart, H. "MRI based Segmentation of Pelvic Bone for Evaluation of Pelvic Organ Prolapse". IEEE Journal of Biomedical and Health Informatics. (In Press)

Onal, S., Lai-Yuen, S., Bao, P., Weitzenfeld, A., Stuart, H. "Image based measurements for evaluation of pelvic organ prolapse". Journal of Biomedical Science and Engineering (JBiSE), 2013. 6 (1): p 45-55.

Onal, S., Lai-Yuen, S, Bao, P., Weitzenfeld, A., Hart, S. (2013) "Pubic Bone Segmentation for Diagnosis of Pelvic Organ Prolapse". 6th Annual College of Engineering Research Day, November 6, Tampa, Fla.

Onal, S., Lai-Yuen, S, Bao, P., Weitzenfeld, A., Greene, K., Hart, S. (2013) "Image Based Measurements for Evaluation of Pelvic Organ Prolapse". AUGS 34th. Annual Scientific Meeting, October 16-19, Las Vegas, Nev.

Onal, S., Lai-Yuen, S, Bao, P., Weitzenfeld, A., Hart, S. (2013) "Combined Supervised and Unsupervised Segmentation of Pubic Bone for Diagnosis of Pelvic Organ Prolapse" INFORMS Annual Meeting, October 6-9, Minneapolis, Minn.

Onal, S., Lai-Yuen, S, Bao, P., Weitzenfeld, A., Greene, K., Hart, S. (2013) "Image Based Measurements for Evaluation of Pelvic Organ Prolapse". 38th. Annual Meeting—International Urogynecological Association, May 28-June 1, Dublin, Ireland Onal, S., Lai-Yuen, S, Bao, P., Weitzenfeld, A., Hart, S. (2013) "MRI-based Segmentation of Pubic Bone for Evaluation of Pelvic Organ Prolapse". Graduate Student and Postdoctoral Scholar Research Symposium, March 25, Tampa, Fla.

Onal, S., Lai-Yuen, S, Bao, P., Weitzenfeld, A., Hogue, D., Hart, S. (28 Nov. 2014) "Quantitative assessment of new MRI-based measurement to differentiate low and high stages of pelvic organ prolapse using support vector machines". Int Urogynecol J, 26:707-713.

Accordingly, what is needed is an automated analysis of medical images to facilitate rapid and accurate diagnosis of pelvic organ prolapse. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved methodology for predicting or diagnosing POP is now met by a new, useful, and nonobvious invention.

In an embodiment, the current invention is a method of predicting or diagnosing pelvic organ prolapse. Alternatively, the current invention is a tangible, non-transitory, computer-readable storage medium having computer-executable instructions for a computer processor to perform a method for predicting or diagnosing pelvic organ prolapse. In either case, the method includes providing, inputting, obtaining, or otherwise receiving a patient's pelvic MRI image that may have a low level contrast intensity (and as such difficult to identify particular regions and structures therein). The bladder and rectum are identified within the MRI image (e.g., based on their intensity values on the MRI image), as is the pubic bone of the patient. Identification of the pubic bone includes extracting and identifying keypoints on the pubic bone and on a pelvic floor on the MRI image based on a spatial relationship between the pelvic organs and the pubic bone structures. Candidate bounding boxes are generated substantially around the pubic bone structures.

Features within the bounding boxes are extracted (e.g., using 2D box and texture features in order to enhance features of the pubic bone structures), and the bounding boxes are classified using a classifier having a learning algorithm (e.g., SVM) that analyzes data used for classification analysis. The extracted features may include gray level features, such that texture features can be extracted using gray level co-occurrence matrix. The coccyx and sacral promontory are then identified via a non-linear regression, using locations of the bladder, rectum, and pubic bone structures to localize the coccyx and sacral promontory. All of this extracted information is combined/fused/linked with clinical information (global information, demographic information, prior shape information, etc.) to predict or diagnose POP.

Identifying the bladder and rectum can be done using a bisecting k-means clustering and morphological opening operations to identify pelvic organs, including the bladder and rectum. The value of k the k-means cluster may be four (4), representing the bone, cartilage, soft tissue and organ, and background regions. In this case, leak detection can be performed to remove clustered cartilage during classification of the bounding boxes. The k-means clustering can also identify the cartilage region and the texture-based classification can identify the bone region, wherein the cartilage and bone regions are combined to find reference points for assessing POP. Alternatively or in addition, identifying the bladder and rectum can include reducing noise and adjusting contrast in the MRI image to normalize the MRI image. In this case, noise is reduced by applying a convolution operation onto the MRI image with smoothing kernel.

The keypoints on the pelvic floor may be corner points on said MRI image, such that said corner points can be extracted using a corner point detector. The bounding boxes may be centered at the keypoints, and a size of each bounding box can be based on a mean shape of the pubic bone as determined by the clinical information. If a keypoint is positioned near a boundary of a corresponding bounding box, which thus does not completely enclose an underlying pubic bone structure, the bounding boxes that do completely enclose underlying pubic bone structures are identified by analyzing each bounding box based on Haar-like and texture features. Between identifying and extracting keypoints, any keypoints outside of a vicinity of the bladder and the rectum may be eliminated.

The classifier may be constructed based on a training data set using a support vector machine trained using a radial basis function kernel providing for non-linear decision surface. The training data set may include training features found to be significant using independent significant feature selection and selected using sequential forward selection by k-fold cross-validation. The SVM-based classifier can classify each candidate bounding box as an enclosed pubic bone region or a partially enclosed pubic bone region, where the SVM-based classifier classifies each bounding box with Haar-like and texture features. If the classifier produces any errors, a relaxation stage can be implemented to smooth the classifier's output. This relaxation stage may include a first phase morphological operation that removes misclassified background, a filling operation to fill small gaps, and a thinning operation to remove regions smaller than about 100 pixels.

Non-linear regression may be trained by parameterizing a location of pelvic floor structures with respect to the bladder, rectum, and pubic bone structures. Identifying the coccyx and sacral promontory can be achieves by determining centroids of coccyx and sacral promontory and generating additional bounding boxes substantially around the coccyx and sacral promontory, where these bounding boxes are centered at the centroids.

Keypoints can be further based on any one or more of the following reference lines and angles: the true conjugate line, the obstetric conjugate line, the diagonal conjugate line, the angle between said diagonal conjugate line and a pubococcygeal line (typically for posterior prolapse), and the angle between said obstetric conjugate line and a mid-pubic line (typically for anterior prolapse). The keypoints on the pubic bone can be identified using morphological skeleton operation, and the keypoints on the patient's vertebra can be identified using intersecting point detection. Alternatively or in addition, keypoints on the pubic bone can be identified by segmenting the pubic bone and corresponding cartilage.

It is an object of the instant invention provides a quantitative prediction model to better detect POP while increasing understanding of the relationships between MRI-based features and clinical information. It is another object of the instant invention to set the foundation towards a computer-aided decision support system to enable the fusion of image, clinical, and patient data in order to improve the diagnosis of POP and prevent incorrect surgeries through personalized and evidence-based assessment. This will have an enormous impact on pelvic disorder diagnosis, surgical planning, and treatment. The presented system can also be applied to the automated localization and extraction of MRI features for the diagnosis of other diseases where clinical examination is not adequate.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figures 1A, 1B:
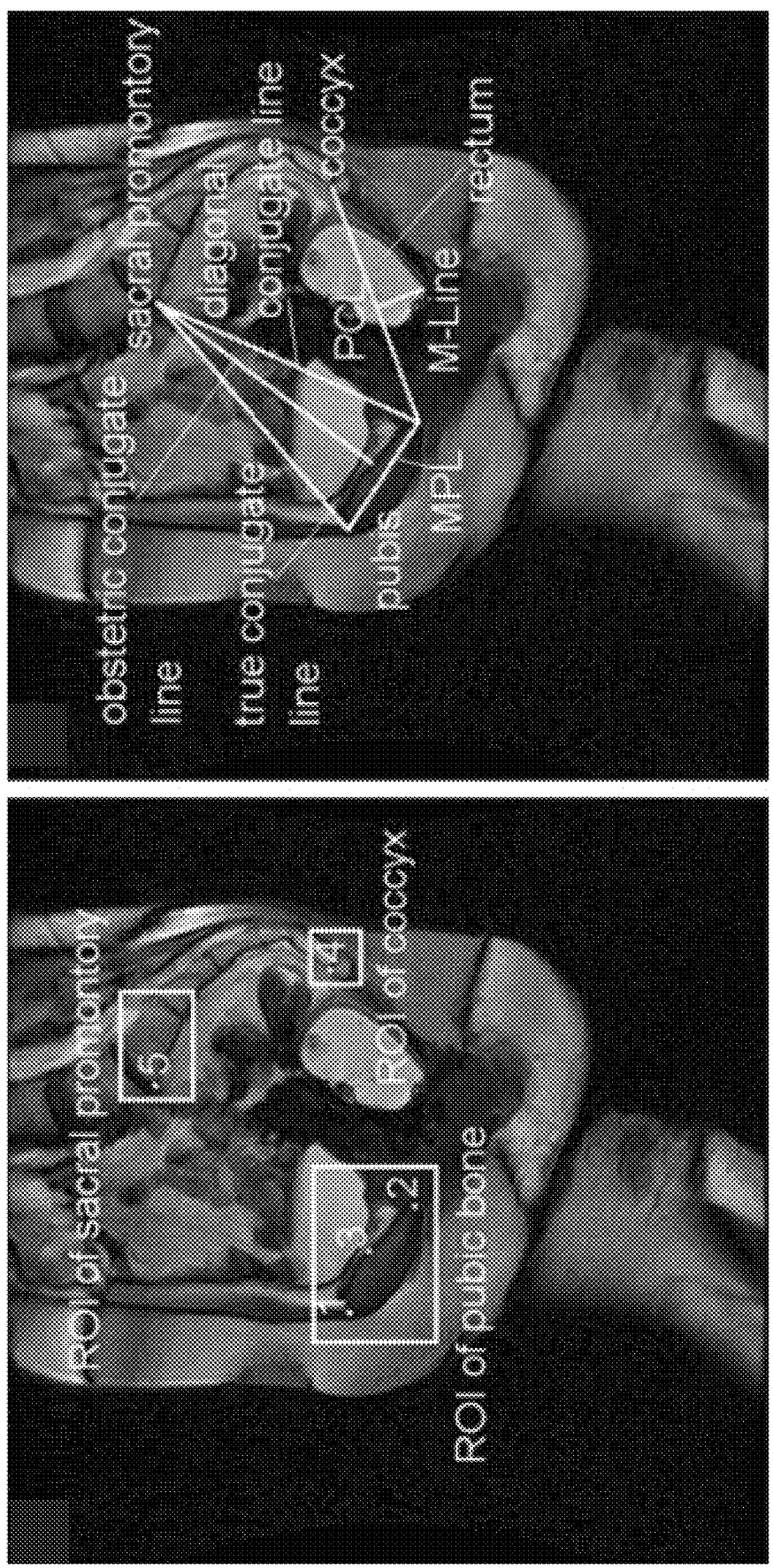
FIG. 1A is a schematic showing the regions of interest.
FIG. 1B is a schematic showing MRI-based features from the conventional art and the current invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

In previous work by the current inventors [7], a framework was presented for semi-automated pubic bone segmentation on MRI. Certain embodiments of the current invention build upon the current inventors' previously developed segmentation technique by addressing the leak detection problem to overcome previously identified issues during the segmentation of structures on images with low contrast and image inhomogeneity. In this example, a multistage method is presented, where the method combines texture-based block classification and clustering analysis using K-means algorithm to identify leak areas. This is performed by subtracting binary images obtained by classification from clustered binary images to effectively segment the bone structure.

In certain embodiments, the current invention is a system that automatically extracts pelvic floor measurements from MRI and fuses them with a wide range of clinical information to facilitate and improve POP diagnosis. In addition to extracting commonly used pelvic floor measurements, the system extracts new image-based features based on new reference lines. Results show that the system can automatically identify reference points for pelvic floor measurements on MRI faster and with more consistency compared to conventional methods, such as manual identification point process by experts. Results also demonstrate that the system achieves higher classification accuracy using the new image-based features compared to using only clinical information/features. Two newly proposed MRI-based features were found to have a significant impact in the prediction of anterior and posterior prolapse. For posterior prolapse, the system significantly increased the prediction accuracy from about 54% to about 84%.

Generally, a system is presented herein that automatically extracts image-based features (e.g., distance between specific, predetermined points and angles) from patient-specific MRI and fuses them with clinical information to assist in the diagnosis of POP. The system automatically finds the location of multiple pelvic floor structures on MRI using a nonlinear regression model with global information. Then, it identifies current and new image-based features using a hybrid supervised and unsupervised segmentation method for bone structures on MRI. These image-based features are fused with patient demographic and clinical information to classify POP cases. This is performed using a prediction model based on support vector machines (SVMs). The system can enable faster, robust, and more consistent automated extraction of features from images with low contrast and high inhomogeneity resulting in more accurate prediction of POP. It also enables the correlation analysis between image-based features and clinical information on large datasets to assist in POP diagnosis.

More specifically, an exemplary segmentation approach is presented herein for automating pelvic bone point identification on MRI. It includes a multi-stage mechanism based on texture-based block classification, leak detection, and prior shape information. Texture-based block classification and clustering analysis using K-means algorithm are integrated to generate the initial bone segmentation and to identify leak areas. Prior shape information is incorporated to obtain the final bone segmentation. Then, the reference points are identified using morphological skeleton operation. Results demonstrate that certain embodiments of the current methodology can achieve higher bone segmentation accuracy compared to conventional segmentation methods. The methodology can also automatically identify reference points faster and with more consistency compared with the manually identified point process by experts. This research aims to enable faster and consistent pelvic measurements on MRI to facilitate and improve the diagnosis of female POP.

I. Segmentation Framework

The pelvic floor measurements process on MRI starts with the identification of reference points, which are located on three different regions: pubic bone, sacral promontory, and coccyx (FIG. 1A). Given that each region has unique characteristics, different approaches have to be considered to identify these points. For instance, points located on the pubic bone can be identified by segmenting the pubic bone and its cartilage. On the other hand, points on the vertebra can be considered as corner points and can be extracted using a corner point detector. Then, the points are connected through lines for pelvic floor measurements.

Figure 2:
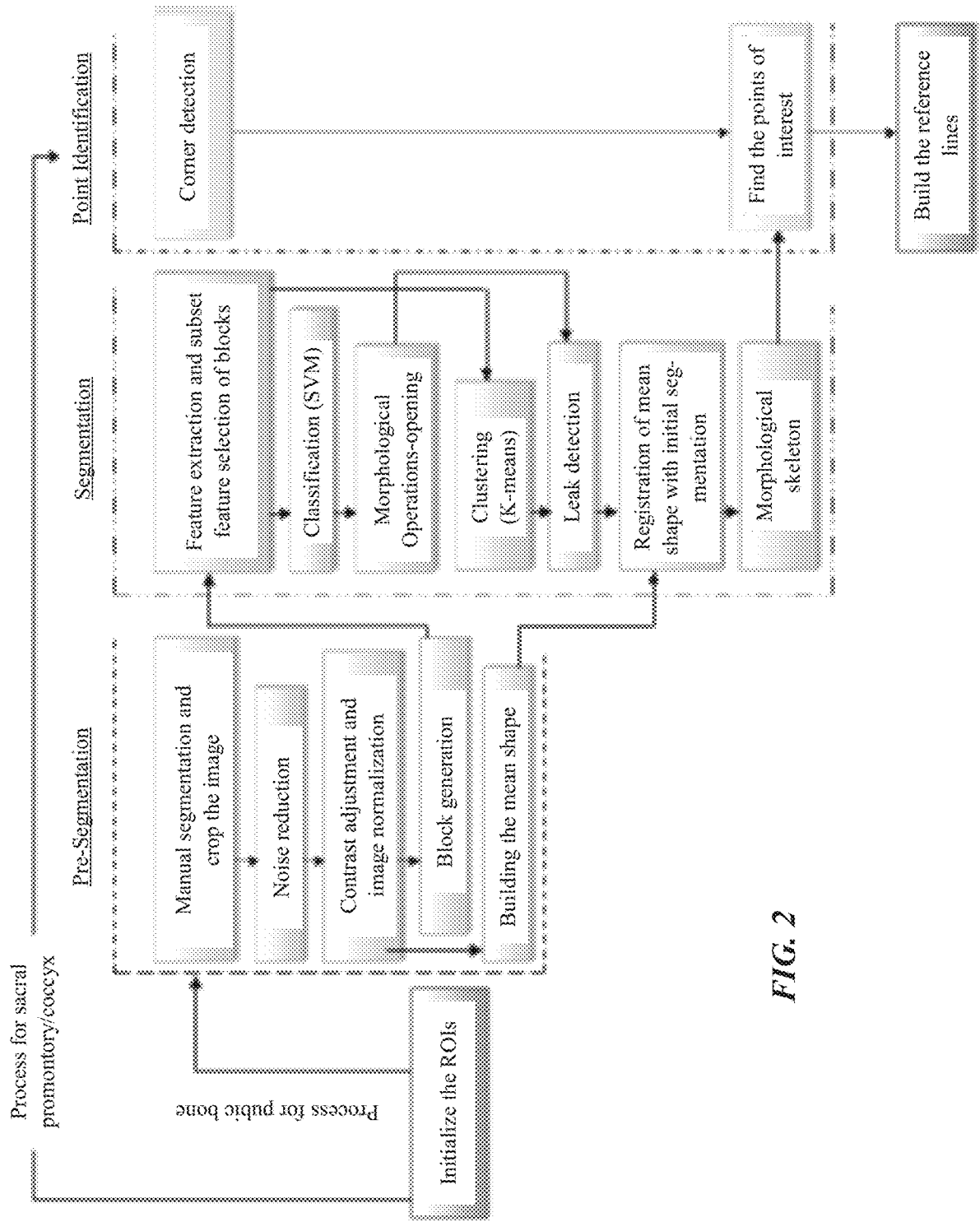
FIG. 2 is an overview of a multi-stage method according to an embodiment of the current invention.

FIG. 2 shows an overview of the current method according to an embodiment of the current invention. It includes three main stages: pre-segmentation, segmentation, and point identification. The methodology begins with noise reduction and contrast adjustment of the images followed by manual segmentation of the pelvic floor structure for data training, and generation of the statistical mean shape. In the approach, each region of interest (ROI) is sub-divided into small blocks of 3×3 pixels to classify them as bone or background blocks and to reduce computational cost. In the segmentation step, feature extraction of the blocks based on intensity and texture features is performed using independent significance feature selection method and sequential forward selection method. Then, blocks are grouped as bone or background blocks using SVMs and K-means clustering to generate the initial segmentation. First phase morphological operation is used to eliminate small regions that do not belong to the bone regions. The segmentation is finalized by incorporating the mean shape into the initial segmentation. In the point identification step, points are identified using skeleton operation and corner point detectors.

A. Pre-Segmentation Stage a. Dataset Description

MR images were obtained from a 3-Tesla GE system (General Electric Company, GE Healthcare, Buckinghamshire, UK) using an 8-channel torso phased-array coil with the patient in a modified dorsal lithotomy position (patient laying in the supine position with their knees slightly elevated and abducted under a support). Dynamic MRI of the pelvic floor structure was obtained using a T2-weighted single-shot turbo spin-echo (SSH-TSE) sequence in the midsagittal plane for 23-27 seconds with a temporal resolution of 2 s (FOV 300×300 $mm^2$, slice thickness 3 mm, TR/TE 2,000/75 ms, 20 image sequences, in-plane resolution of 1.6×1.6 $mm^2$). Subjects were coached, prior to imaging, on performance of an adequate valsalva maneuver (straining maneuver) to observe the movement of the pelvic organs from rest to maximum strain. The image data has been preprocessed and de-identified.

2D dynamic MRI images of 25 patients were analyzed in this study and each patient has 20 image sequences showing the pelvic floor structures from rest to maximum strain. Even though the bone structures are static during the image sequences, the pelvic organs and other soft tissue surrounding the bones are not static and move at each image sequence. For this reason, 20 images of each patient were used to train the model and improve the bone segmentation. Then, after identifying the reference points on the 20 images of each patient, the average of the reference points over the image sequence was calculated.

b. Image Pre-Processing

The first step of the current method is to perform noise reduction by applying the convolution operation onto the raw image with the smoothing kernel. In this study, a Gaussian kernel was used due to its computational efficiency and ability to control the degree of smoothing. The Gaussian kernel is expressed in the discrete form with a size of 3×3 pixels. After noise reduction, image normalization is performed to improve the contrast in the images by stretching the range of intensity values. Minimum and maximum values used for normalization are 0 and 255, respectively.

Prior shape information is acquired by generating the mean shape of the pubic bone (bone and cartilage) from a set of training images, for example as previously discussed. To generate the mean shape, the pubic bone was manually segmented by a radiologist on all the images and the results were stored as a binary mask. Then, the ROI for the pubic bone was cropped through a K×L sized window. The extracted structures were aligned with respect to a set of reference axes to remove the differences in shapes due to translation, scaling, and rotation. An image was selected arbitrarily as the reference shape. Then, the mean shape is created as a binary image as described in the current inventors' previous work [7, 27].

Figure 3:
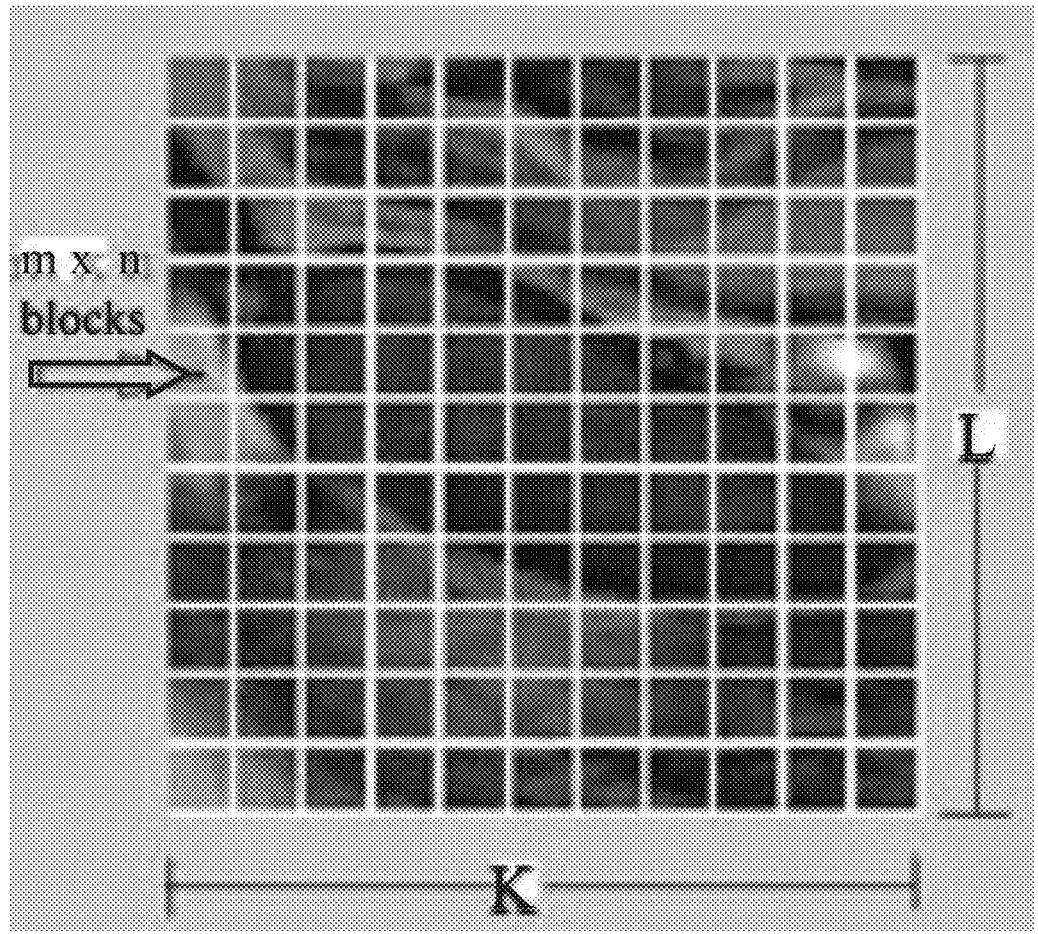
FIG. 3 is a K×L size cropped image (window) and m×n size blocks (blocks are shown larger than 3×3 pixels for demonstration purposes).

Finally, the ROI for the pubic bone is sub-divided into small blocks of m×n size as shown in FIG. 3. These small blocks of pixels will be used for the classification process instead of using individual pixels to increase computational efficiency and to enable the use of texture features for classification.

B. Segmentation Stage a. Feature Extraction

Feature selection is a challenging task in the classification process to differentiate patterns accurately. Due to the low level contrast intensity of MRIs, intensity based features alone do not provide enough information for the classification. For this reason, texture features have been used to improve the classification accuracy on MRI by providing information on the relative position between any two pixels [28]. Medical images possess different textures depending upon the area of the body considered for imaging.

Gray level features are extracted from each block. In addition, gray level co-occurrence matrix (GLCM) is utilized to extract the texture features as in [28]. GLCM provides information on the relative position between two pixels using horizontal left to right direction. Table I shows the intensity and GLCM features used in this study.

TABLE I

Intensity and GLCM features.

| Intensity Features | GLCM Features | |
| --- | --- | --- |
| Average gray level | Autocorrelation | Sum of squares |
| Average contrast | Contrast | Sum average |
| Smoothness | Correlation | Sum variance |
| Skewness | Cluster prominence | Sum entropy |
| Uniformity | Cluster shade | Difference variance |
| Entropy | Dissimilarity energy | Difference entropy |
| | Entropy | Maximum probability |
| | Homogeneity | Info. measure of correlation |

After feature extraction, a two-step feature subset selection is performed. In the first step, irrelevant or redundant features are removed using the independent significance feature selection method as described in [29]. This is used to eliminate features with a significance level lower than 2 as calculated from the following equation:

$$significance_i = \frac{|\text{mean}(Bone_i) - \text{mean}(Background_i)|}{\sqrt{\frac{\text{var}(Bone_i) + \text{var}(Background_i)}{n1 + n2}}} \quad (1)$$

where Bone, represents the $i^{th}$ feature being measured from bone blocks, Background, indicates the $i^{th}$ feature being measured from background blocks, n1 and n2 are the corresponding number of blocks for bone and background, respectively. Based on the significance level, 12 independent significant features were identified in this study.

In the second step of the feature subset selection process, the final set of significant features for training the classifier is selected using the sequential forward selection method measured by 10-fold cross-validation. In 10-fold cross-validation, the feature set was first divided into k subsets of equal size. Each subset is tested on the remaining k–1 subsets using mean squared error that minimizes the mean criterion value. This process continues until the addition of more features does not decrease the criterion any further.

b. Block Classification

The classification of the image blocks involves two steps: construction of the classifier and prediction. In the first step, a classifier structure is constructed based on the training data set using SVMs. Implementation of SVMs is designed to increase the speed of the classification process by classifying blocks of pixels instead of classifying each pixel. SVMs were trained using the "kernel trick", which allows the algorithm to fit the maximum-margin hyper plane in a transformed feature space to provide for non-linear decision surface. The training vectors $x_i$, i=1, 2, ..., L are nonlinearly mapped onto a high-dimensional feature space by $\Phi : \mathbb{IR}^M \mapsto F$ and then a linear separation is attempted in F. If F is a Hilbert space, K is a kernel function in the original space $\mathbb{IR}^M$ that describes the inner product in F.

$$\Phi(u) \cdot \Phi(v) = K(u,v) = (u \cdot v + 1)^2 \quad (2)$$

where K(u,v) should satisfy Mercer's condition that ensures that the kernel function can always be expressed as the dot product between two input vectors in high dimensional space. This transformed space of the SVM kernels is called a reproducing kernel Hilbert space. The Radial Basis Function kernel (RBF) was employed in the training process to construct non-linear SVMs and is described as follows:

$$K(u,v) = \exp(-\gamma \|u-v\|^2) \quad (3)$$

Figures 4A, 4B, 4C, 4D:
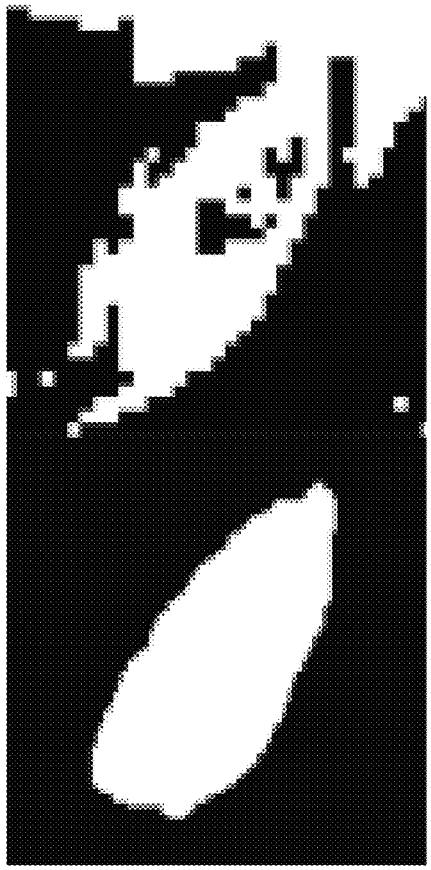
FIG. 4A depicts a portion of the segmentation process, specifically the ground truth image.
FIG. 4B depicts a portion of the segmentation process, specifically the block classification ($R_{class}$) with bone (white) and background (black).
FIG. 4C depicts a portion of the segmentation process, specifically the first phase classified image with morphological operations ($R_{class+morph}$).
FIG. 4D depicts a portion of the segmentation process, specifically the clustering $R_{cluster}$ with cartilage (white) and background (black).

There are two parameters for an RBF kernel that need to be determined: C representing the penalty parameter and $\gamma$ representing the RBF sigma parameter. 10-fold cross validation is used to in this study to identify the best (C,$\gamma$) so that the classifier can accurately predict unknown data. After the blocks are trained according to the selected features, the second step of the segmentation process is to apply the model to test example images using the built SVM classifier. The anticipated outcome, $R_{class}$, at the end of this process is a set of two groups of blocks that are automatically classified as bone (white) and background (black) as shown in FIG. 4B.

The classification method evaluates each block independently based on the selected features. Since the classifier may produce errors, a relaxation stage is needed to smooth the classifier's output. Therefore, first phase morphological operations are applied to the classifier's output to remove the misclassified background blocks. To fill the small gaps on the objects, the filling operation is incorporated and then small regions that are fewer than 100 pixels are removed using "thinning" followed by the area opening operation. Image opening is done by using "diamond" structuring element that has a radius of 4. The result, $R_{class*morph}$, is shown in FIG. 4C.

c. Block Clustering

Given the similar intensity characteristics of bone and soft tissue, soft tissue regions may be occasionally included into the bone region. This problem, considered as "leaks", occurs when the pubic bone and background regions (soft tissue, cartilage and fat regions) become joined together due to the lack of strong edges between them.

A leak detection approach is discussed herein, where the approach is based on integrating SVM classification and K-means clustering. K-means clustering is used since it is convenient for medical images as the number of clusters (K) is usually known for particular regions of human anatomy [30]. The region of the pubic bone can be divided into four sub-regions representing the bone, cartilage, fat, and background. Therefore, K is selected to be 4 in this study. Since the basic K-means clustering is susceptible to initialization, a "bisecting K-means" algorithm presented in [31] was used. The idea is to obtain K clusters by first splitting the set of all points into two clusters. Then, one of these clusters is selected for splitting and the process continues until K clusters are generated. The bisecting K-means algorithm is less dependent on initialization because it performs several trial bisections and takes the one with the lowest sum of the squared error (SSE). The outcome of this process is the region called $R_{cluster}$.

d. Leak Detection and Registration

Figure 4H:
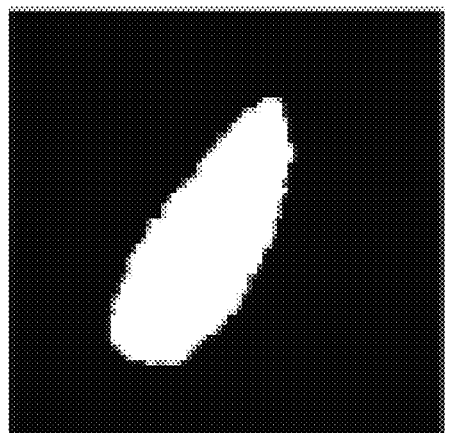
FIG. 4H depicts a portion of the segmentation process, specifically the first registration between f and g ($R_{intal}$).
Figure 4G:
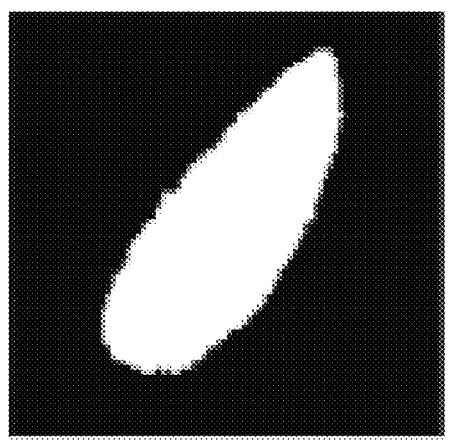
FIG. 4G depicts a portion of the segmentation process, specifically the mean shape ($R_{meanshpe}$).

After clustering the blocks, the cluster that represents the cartilage is selected to identify the leak as shown in FIG. 4D. The clustered cartilage region $R_{cluster}$ is subtracted from the classified region after first morphological operation $R_{class+morph}$ to find the leakage area $R_{leakage}$ as seen in FIG. 4E (black region). Their complement $R_{complement}$ is shown in FIG. 4F (white region), and is calculated as follows:

$$R_{complement} = (R_{class+morph} - R_{cluster})(i,j) \geq 1 \quad (4)$$

where, $$R_{leakage} = (R_{class+morph} - R_{cluster})(i,j) < 0 \quad (5)$$

Figure 4F:
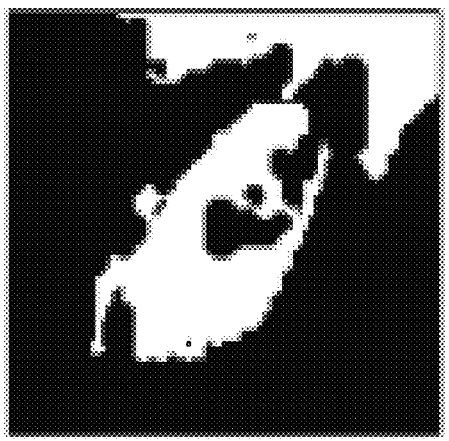
FIG. 4F depicts a portion of the segmentation process, specifically the $R_{complement}$.
Figure 4E:
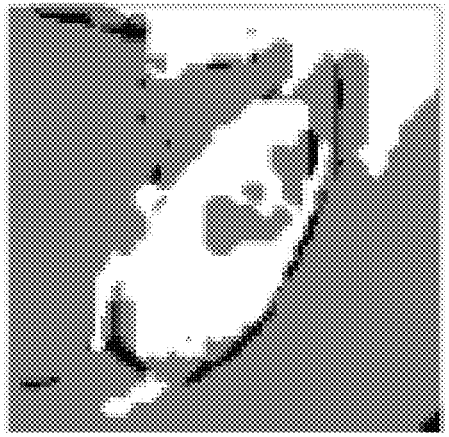
FIG. 4E depicts a portion of the segmentation process, specifically the leakage region detected (black area).

As shown in FIG. 4F, the region $R_{complement}$ provides separated regions that include the desired bone region, and the soft tissue and fat regions. $R_{complement}$ is edited by incorporating the statistical mean shape, $R_{meanshape}$, as shown in FIG. 4G. $R_{meanshape}$ is registered with the $R_{complement}$ by using similarity type image registration that considers rotation, translation and scaling as shown in FIG. 4H. The initialization problem was eliminated by using the largest component in $R_{complement}$ that corresponds to the bone structure. Any small regions surrounding the bone structure were removed by morphological opening operations in the previous steps. The mean square error metric was used as a similarity metric and step gradient descent approach was used for minimization. This results in the initial segmentation region $R_{initial}$.

$$R_{initial} = (R_{meanshape} \xleftrightarrow{\text{Transform}} R_{complement}) \quad (6)$$

Figure 4K:
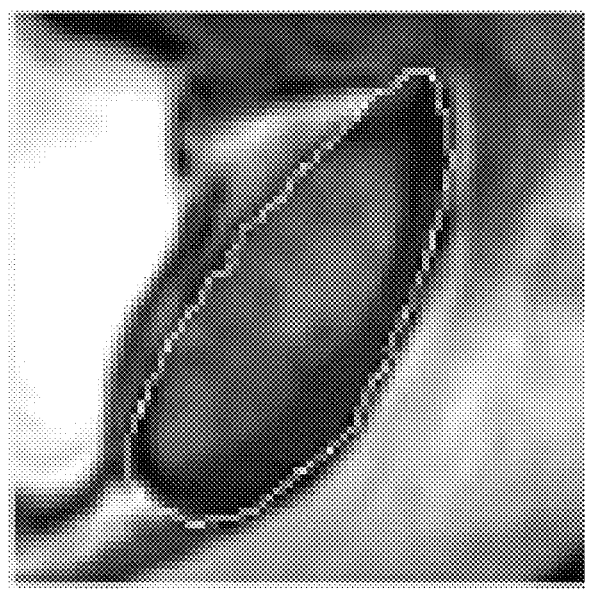
FIG. 4K depicts a portion of the segmentation process, specifically the final segmentation of pubic bone.
Figure 4J:
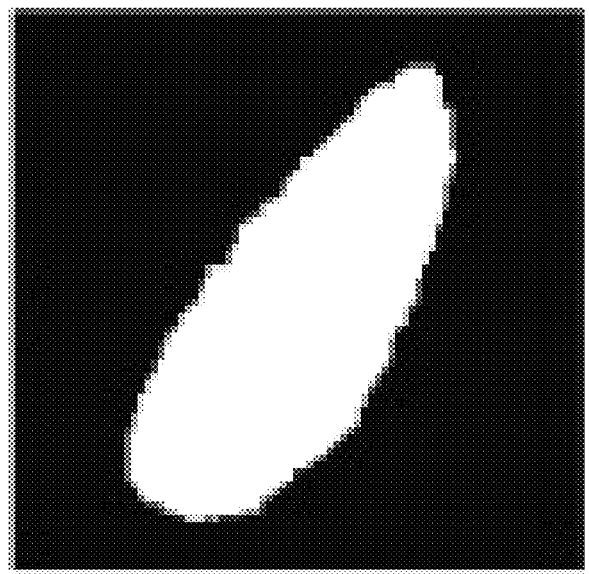
FIG. 4J depicts a portion of the segmentation process, specifically the final registration between g and i ($R_{final}$).
Figure 4I:
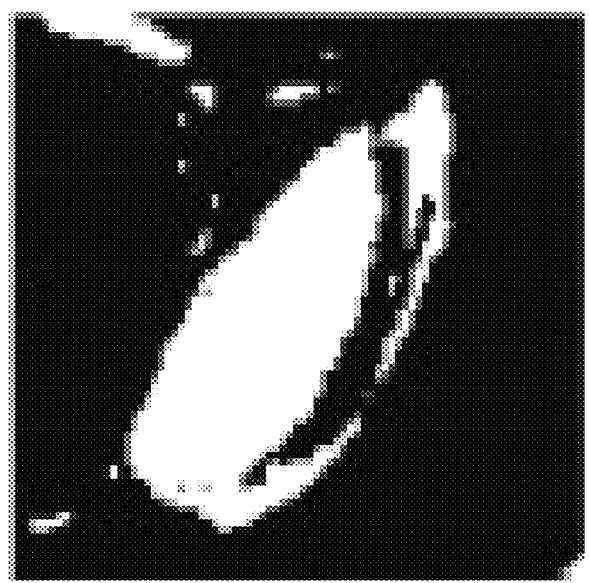
FIG. 4I depicts a portion of the segmentation process, specifically the union of d and h ($R_{initial+cluster}$).
Figure 4L:
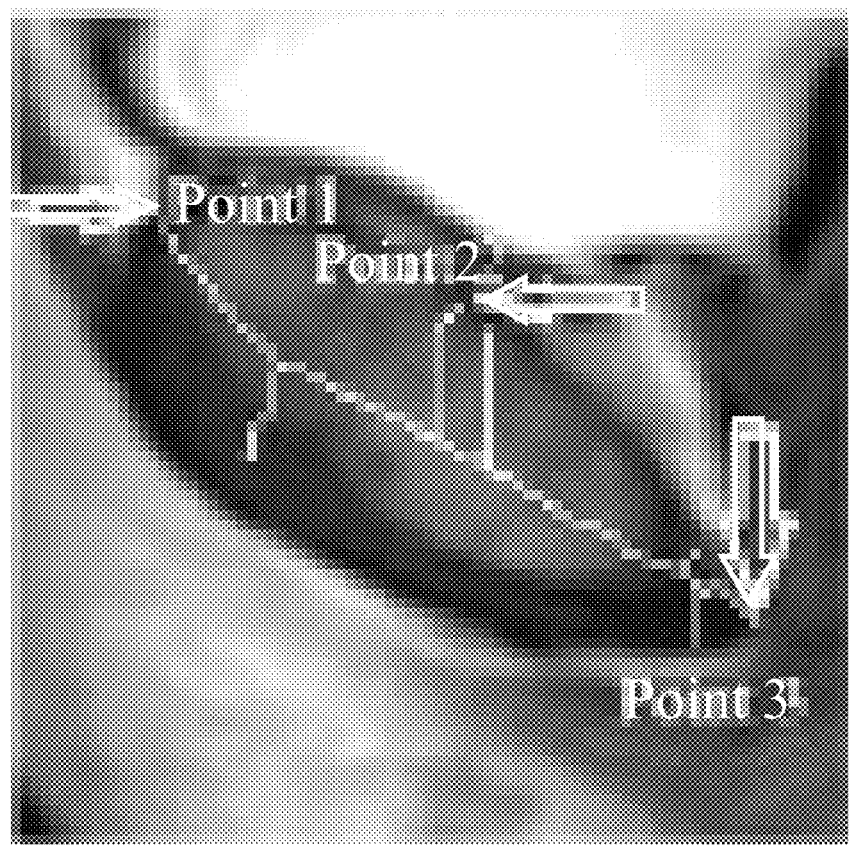
FIG. 4L depicts a portion of the segmentation process, specifically the morphological skeleton of final segmentation.

Then, as shown in FIG. 4I, the correction step involves adding the cartilage region $R_{cluster}$ to $R_{initial}$ to obtain the preliminary region of the pubic bone $R_{initial+cluster}$. The current procedure for identifying the pelvic floor reference points on MRI is based on the pubic bone and its cartilage (bone+cartilage). For this reason, a goal is to identify both the pubic bone and its cartilage to determine the corresponding reference points automatically. k-means clustering is employed to find the cartilage region and the texture-based classification provides the bone structure region. Therefore, the two regions were combined to obtain the full bone+ cartilage region to find the reference points for assessing POP. Finally, a second registration is performed between the corrected image, $R_{initial+cluster}$ and the mean shape, $R_{meanshape}$, with the same similarity type image registration. At the end of this process, the final segmentation of the pubic bone is obtained, $R_{final}$, as shown in FIG. 4J. Then, the boundary of the pubic bone is extracted as shown FIG. 4K. This will be used to identify the reference points using the morphological skeleton operation as indicated in FIG. 4L.

$$R_{final} = (R_{meanshape} \xleftrightarrow{\text{Transform}} R_{initial+cluster}) \quad (7)$$

C. Point Identification Stage

Figure 5A:
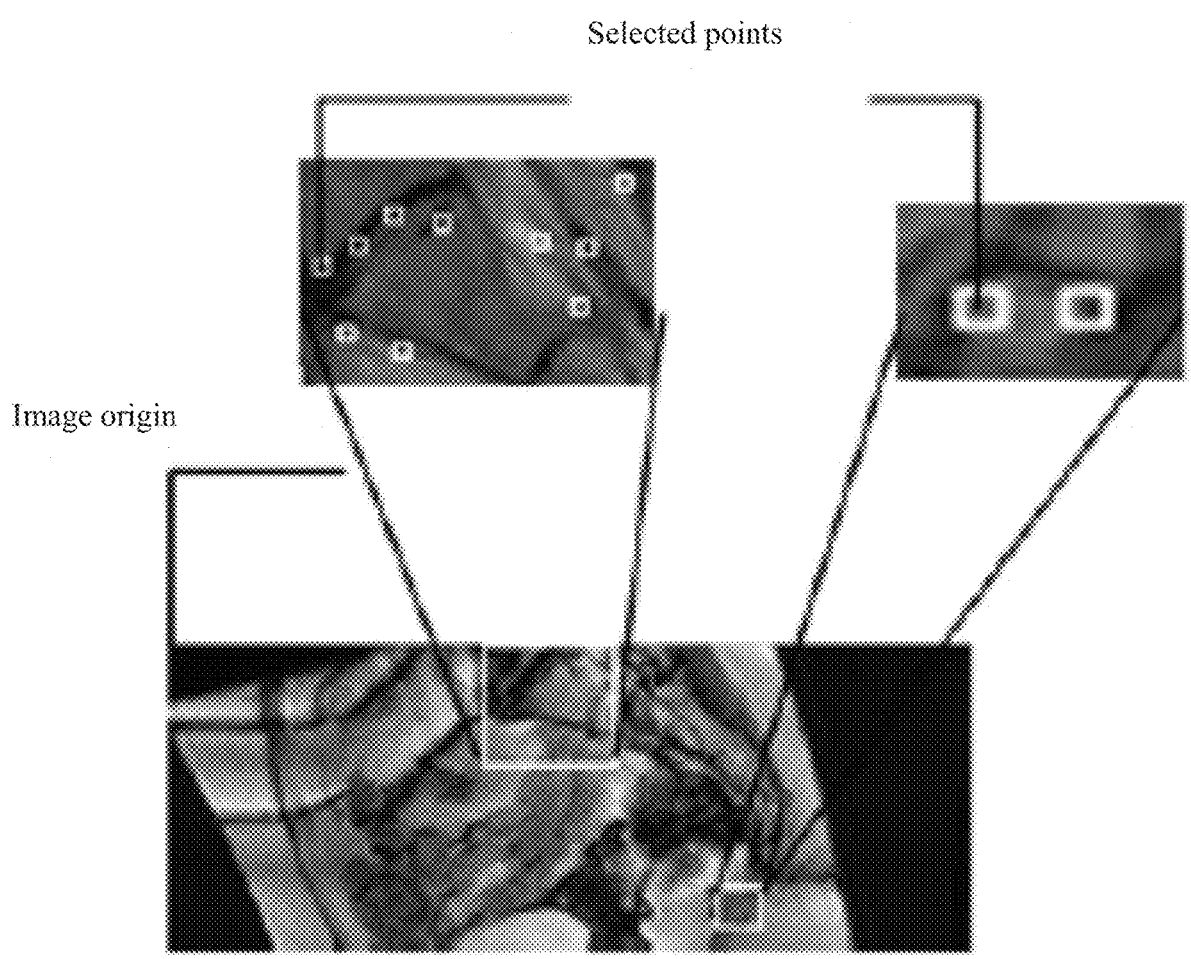
FIG. 5A shows reference bony joints for sacral promontory and coccyx.

After segmentation, the reference points located on the pubic bone can be found using the morphological skeleton operation, which removes pixels on the boundaries of the pubic bone and provides at least three branches of the skeleton without allowing the object to break apart. The remaining pixels constitute the image skeleton, whose extreme points indicate the reference points 1, 2 and 3. For reference points 4 and 5, these can be defined as corner points for which there are two dominant and different edge directions on the local neighborhood of the point. Consequently, these points can be detected using a corner point detector such as the Harris corner detection algorithm [32] as presented in the current inventors' previous work [7] and shown in FIG. 5A.

Figure 5B:
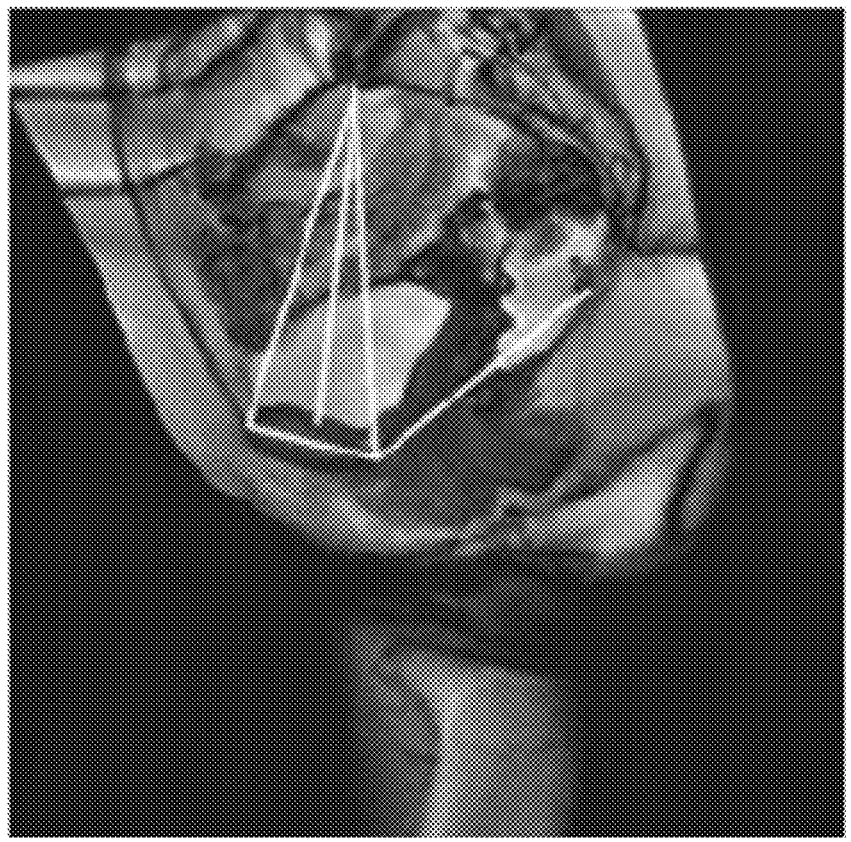
FIG. 5B shows the pelvic floor reference points and lines generated by the current methodology.
Figure 6A:
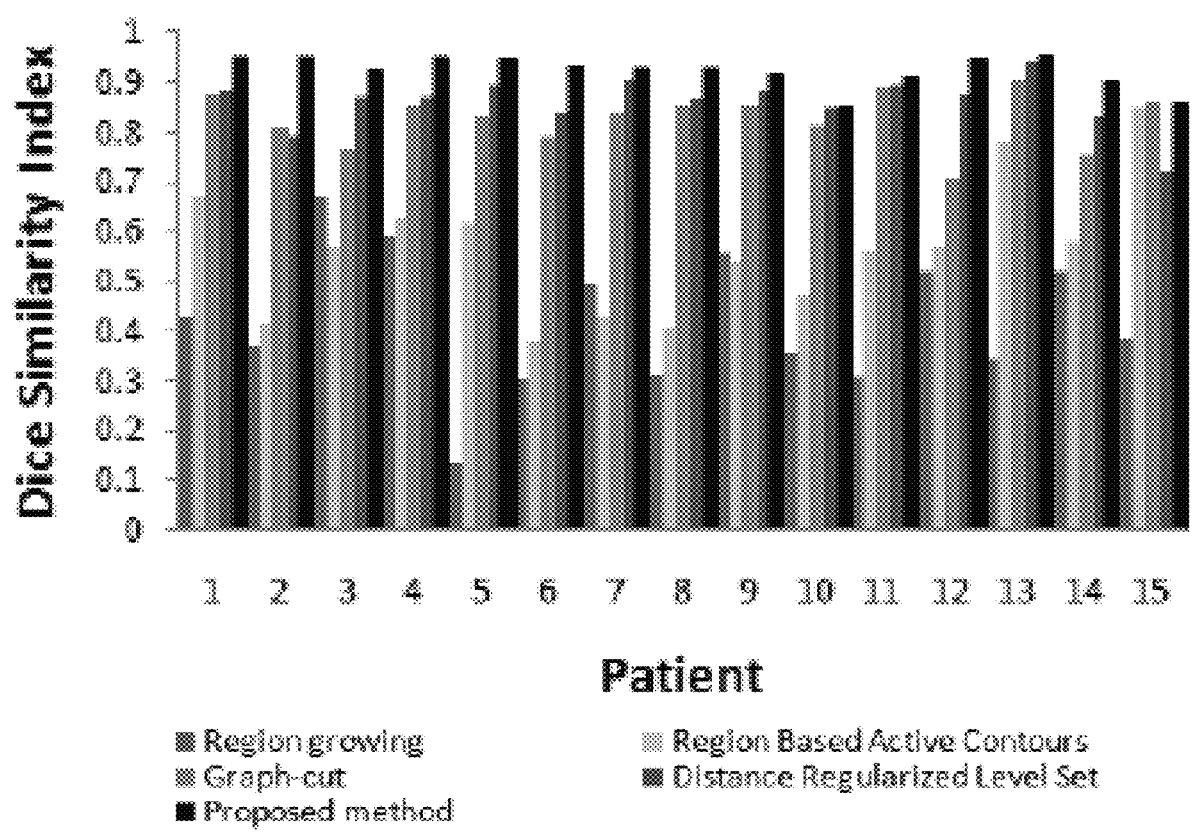
FIG. 6A is a comparison of performance of the current methodology with conventional dice similarity index methodology.
Figure 6B:
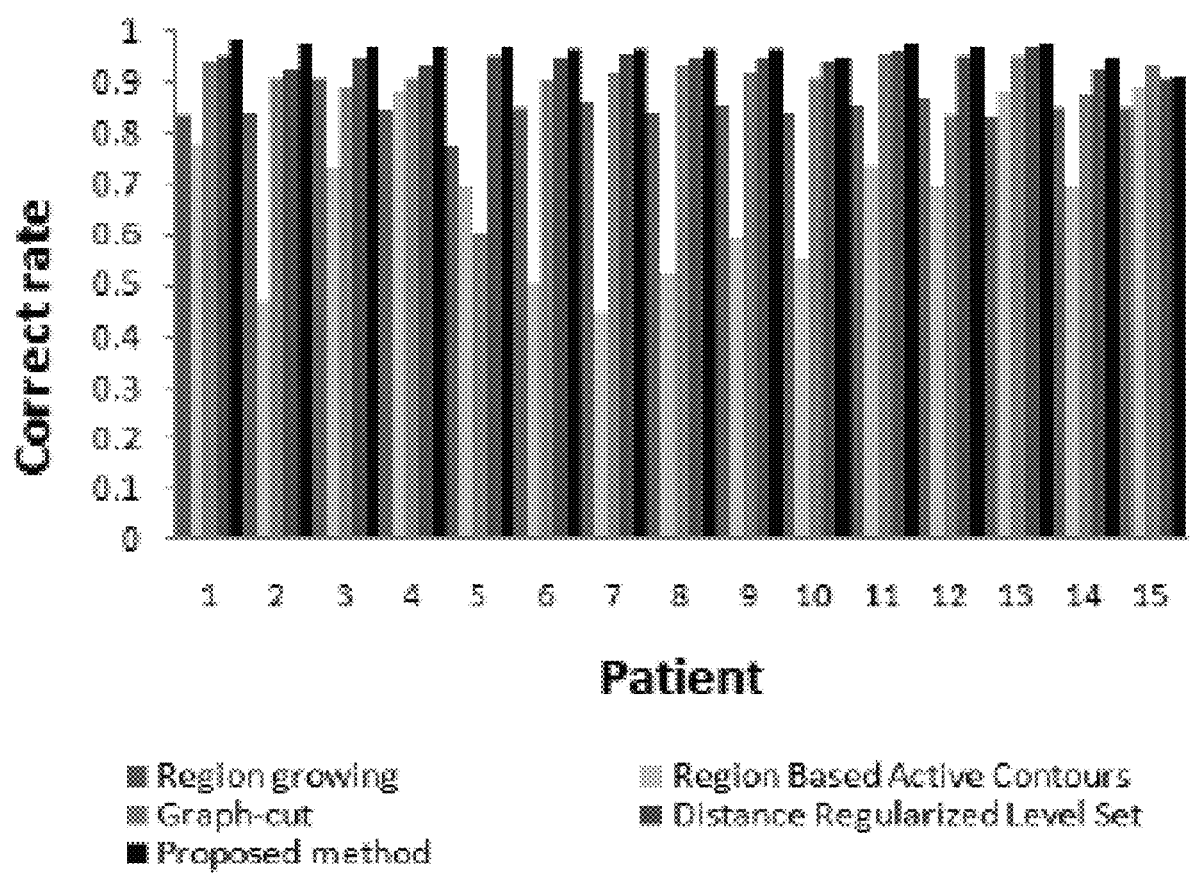
FIG. 6B is a comparison of performance of the current methodology with conventional correct rate methodology.
Figure 6C:
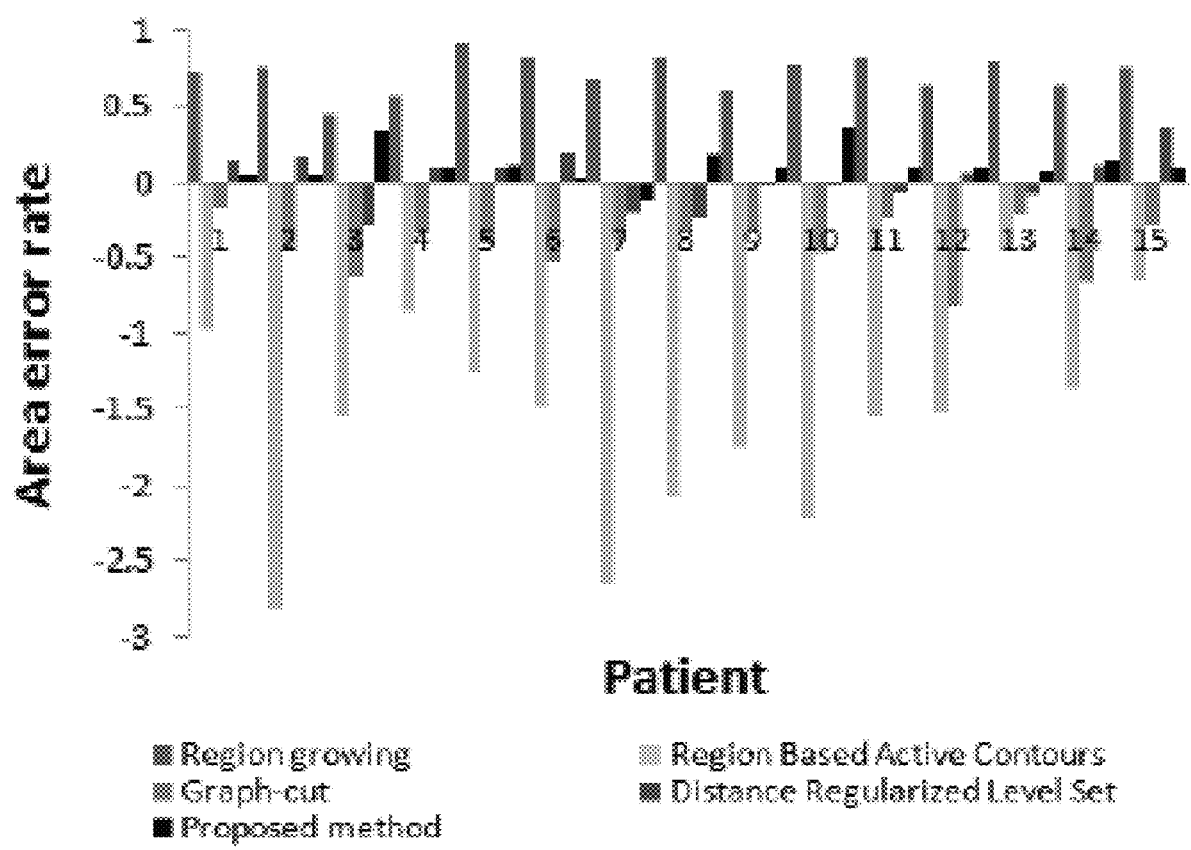
FIG. 6C is a comparison of performance of the current methodology with conventional area error measure methodology.
Figure 6D:
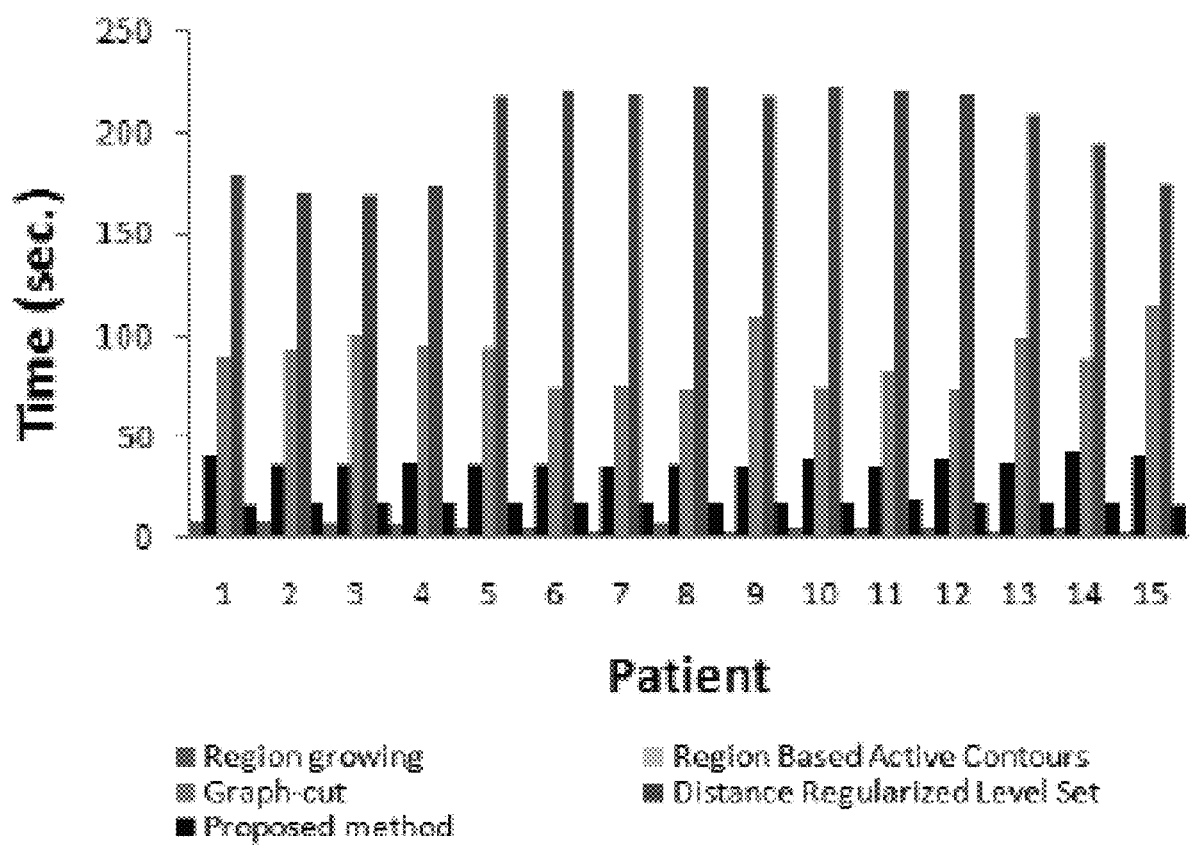
FIG. 6D is a comparison of performance of the current methodology with conventional computation time methodology.

After identifying all the reference points, they are moved onto the original MR image and used to generate the reference lines as shown in FIG. 5B. These points can also be used to build other reference lines such as Diagonal, Obstetric and True Conjugate lines, which could possibly be used for radiological assessment of POP.

Validation of Methodology

The validation of the current method was performed on a representative clinical data set of 25 dynamic MRI. The database was divided into a training set of 10 randomly selected images and a testing set composed of the remaining 15 images. The dynamic MRI of each patient included 20 image sequences. The current methodology was implemented using MATLAB 2012b on a workstation with 3.00 GHz dual processors and 2 GB RAM.

I. Bone Segmentation

The performance of the segmentation method was measured by quantifying the region overlap between the manual and automated segmentations using the Dice Similarity Index (DSI) [25]. In addition to DSI, two additional measures were used: correct rate and area error measure (AEM) [33]. First, the segmentation results from the current method were compared to the results from the texture-based classification method only as shown in Table II. The texture-based classification method is about 6 seconds faster than the current method. However, the segmentation accuracy of the texture-based classification is very low with DSI and correct rate of 52% and 79%, respectively. It was also observed that the segmented regions obtained with the classification only method resulted in over-segmentation in most of the cases. The area error measure should be 0 for a perfect segmentation. The classification only method also resulted in more negative values indicating that the segmented regions are larger than the manually segmented regions. On the other hand, the current method with the leak detection algorithm provides higher accuracy for all cases with a DSI above 92% for thirteen cases and a correct rate above 95% for all cases.

In order to verify the quality of the current segmentation technique, the current method was compared with four commonly used segmentation methods in medical image segmentation: region growing [11], region based active contour [14], graph-cut [23], and distance regularized level set [15]. In the study, the Taguchi method [34] was used to analyze the significance of each variable in the performance of the segmentation processes. The following lists the parameters used:

Region growing: Absolute threshold level to be included: 10; maximum distance to the initial position: 20.

Region based active contour: Alpha: 0.2; Max iteration: 250

Graph-cut: 10 seeds for background and 10 seeds for foreground; Large constant, K=10; Similarity variance, sigma=; Terminal Constant, lambda=$10^{12}$; Similarity Constant, c=$10^8$ Distance regularized level set: Time step=1; Coefficient of the distance regularization, mu=0.2/time step; Inner iteration=10; Outer iteration=30; Coefficient of the weighted length, lambda=5; Coefficient of the weighted area, alpha=−3; Parameter that specifies the width epsilon=1.5

TABLE II

Performance comparison of the instant method with classification method only.

| | DSI | | Correct rate | | AEM | | Time (sec) | |
|---|---|---|---|---|---|---|---|---|
| | Classification | Instant method | Classification | Instant method | Classification | Instant method | Classification | Instant method |
| 1 | 0.73 | 0.946 | 0.869 | 0.976 | −0.127 | 0.063 | 11.2 | 17.2 |
| 2 | 0.484 | 0.947 | 0.729 | 0.978 | −0.801 | 0.051 | 12 | 18.2 |
| 3 | 0.755 | 0.919 | 0.889 | 0.97 | −0.561 | 0.341 | 10.7 | 17.9 |
| 4 | 0.592 | 0.948 | 0.824 | 0.973 | 0.343 | 0.091 | 11.1 | 18.2 |
| 5 | 0.703 | 0.943 | 0.835 | 0.972 | −0.287 | 0.109 | 15.2 | 17.8 |
| 6 | 0.38 | 0.931 | 0.792 | 0.969 | 0.109 | 0.026 | 12.05 | 18.4 |
| 7 | 0.683 | 0.924 | 0.823 | 0.968 | −0.686 | −0.106 | 11.3 | 18.1 |
| 8 | 0.352 | 0.926 | 0.692 | 0.964 | −0.429 | 0.18 | 13.4 | 17.9 |
| 9 | 0.695 | 0.917 | 0.799 | 0.967 | −0.833 | 0.102 | 12.1 | 18.2 |
| 10 | 0.658 | 0.851 | 0.804 | 0.948 | −0.848 | 0.368 | 11.7 | 18.5 |

TABLE II-continued

Performance comparison of the instant method with classification method only.

| | DSI | | Correct rate | | AEM | | Time (sec) | |
|---|---|---|---|---|---|---|---|---|
| | Classification | Instant method | Classification | Instant method | Classification | Instant method | Classification | Instant method |
| 11 | 0.373 | 0.912 | 0.833 | 0.978 | 0.447 | 0.098 | 13.5 | 18.6 |
| 11 | 0.799 | 0.943 | 0.904 | 0.974 | −0.368 | 0.102 | 14.2 | 17.5 |
| 12 | 0.569 | 0.952 | 0.831 | 0.978 | 0.186 | 0.082 | 12.6 | 17.9 |
| 13 | 0.776 | 0.902 | 0.876 | 0.946 | −0.419 | 0.154 | 12.4 | 18.5 |
| 14 | 0.534 | 0.856 | 0.736 | 0.912 | −0.864 | 0.102 | 11.2 | 17.2 |

As shown in FIG. 6, the region growing method is the fastest segmentation method; however, its segmentation accuracy is the lowest among the methods, with approximately 30% in DSI and 80% in correct rate. It can also be observed that the segmented regions from the region growing method are smaller than the manually segmented regions for all cases. The graph-cut and distance regularized level set methods provide better results than the region growing and region based active contour for all cases in terms of DSI and correct rate. However, both methods have drawbacks such as longer computational time, initialization sensitivity, and the need to select the best parameters. The area error measure rates for these methods are also very low compared to the region growing and active contour methods.

The current method provides the highest accuracy with above 92% in DSI for thirteen cases and above 95% in correct rate metric for all cases. In terms of computational time, the current method is the second fastest method. Results also show that the current method only has one case with over-segmentation but with very low error rate. Only two cases provided a smaller region when compared with the manually segmented region. These results demonstrate that the current segmentation technique achieves higher segmentation accuracy and performance compared to conventional segmentation methods.

II. Reference Points Identification

The current method was used to identify the pelvic bone and its reference points (p1, p2, and p3) and the reference points on the vertebra (p4 and p5) on the testing images. The point locations identified by the current method were compared with the points identified manually by three experts over three iterations. The average of the three iterations is calculated to find the experts' average point location. Table III shows the standard deviation of each point identified by the experts over all the fifteen images. It can be observed that the manual identification of p4 vastly differs among the experts due to difficulties in identifying the coccyx on the images. Interobserver reliability was also assessed by calculating the intraclass correlation coefficient (ICC) for all five reference points. An ICC>0.9 indicates excellent agreement, between 0.9 and 0.6 good agreement, between 0.6 and 0.4 moderate agreement, and <0.4 poor agreement. Table IV provides the Hausdorff distance and the mean distance between the point locations identified by the current method and by experts.

TABLE III

Min and max standard deviation of reference points on all trials on 15 patients performed by 3 experts.

| | Standard deviation (in mm) by manual identification | | | |
|---|---|---|---|---|
| Point | x | y | ICC | CI 95% |
| p1 | [0.31-4.52] | [0.22-4.37] | 0.95 | (0.94-0.96) |
| p2 | [0.13-3.08] | [0.37-3.64] | 0.98 | (0.97-0.99) |
| p3 | [0.63-6.47] | [0.83-4.12] | 0.98 | (0.96-0.98) |
| p4 | [2.01-21.04] | [4.37-26.87] | 0.81 | (0.79-0.94) |
| p5 | [0.38-27.19] | [1.01-20.12] | 0.87 | (0.94-0.98) |

TABLE IV

Hausdorff distance and mean distance between point locations by experts and by the instant method.

| Point | Hausdorff distance (mm) | Mean distance (mm) |
|---|---|---|
| p1 | 4.12 | 1.10 |
| p2 | 10.19 | 2.13 |
| p3 | 6.08 | 1.93 |
| p4 | 14.42 | 4.00 |
| p5 | 8.54 | 2.40 |

TABLE V

Euclidian distance in mm between points identified manually and using the instant method for 15 patients.

| | P1 | P2 | P3 | P4 | P5 | P6 | P7 | P8 | P9 | P10 | P11 | P12 | P13 | P14 | P15 |
|---|---|---|---|---|---|---|---|---|---|---|---|---|---|---|---|
| p1 | 1.5 | 1.3 | 3.3 | 3.2 | 3.9 | 6.9 | 6.8 | 2.1 | 5.4 | 3.7 | 0.9 | 6.9 | 3.5 | 5.2 | 0.9 |
| p2 | 7.0 | 16.3 | 3.8 | 3.0 | 1.9 | 3.2 | 3.4 | 5.6 | 4.7 | 14.9 | 8.2 | 4.1 | 1.4 | 1.2 | 0.9 |
| p3 | 5.6 | 3.9 | 3.0 | 2.3 | 11.2 | 9.6 | 5.3 | 9.9 | 7.5 | 3.0 | 2.4 | 3.0 | 3.9 | 2.6 | 2.7 |
| p4 | 14.8 | 24.3 | 7.6 | 5.3 | 5.3 | 9.8 | 12.3 | 2.9 | 5.7 | 6.4 | 9.4 | 17.4 | 8.8 | 1.1 | 3.8 |
| p5 | 8.7 | 10.7 | 9.6 | 6.5 | 4.1 | 7.3 | 1.1 | 3.3 | 3.6 | 5.8 | 2.8 | 4.2 | 5.7 | 1.8 | 7.0 |

The accuracy of the automatically identified points by the current method was compared to the average location of the manually identified points, where the Euclidian distance is calculated between the manually and automatically identified points as shown in Table V. It can be observed that the current method is able to accurately identify all the reference points. In terms of computation time, the manual point identification process for each patient that has 20 image sequences was about 10 minutes while the current method took 4.5 minutes.

III. Discussion

In this study, a segmentation approach is presented that provides leak detection for automating pelvic bone point identification on MRI. Results demonstrate that the current method achieves higher bone segmentation accuracy compared to conventional segmentation methods. The current method can also automatically identify reference points faster and with more consistency compared with the manually identified point process by experts.

When analyzing the intra-observer reliability for reference point identification amongst the three experts, there were no significant difference found between measurements taken by the three experts for p1, p2, and p3. There was also good agreement found but high standard deviation for p4 and p5. On the other hand, the current method is fully deterministic, i.e., it can identify the exact same location for each reference point for all the cases.

As seen in Table V, the lowest accuracy obtained by the current method was related to p4 and p5. This was due to the anatomical location of these points, which are not easily identifiable on the images in most cases. These differences can be related to the results in Table III, where p4 and p5 had the highest standard deviation among experts. It can also be observed that the current method provided better results for some patients (e.g., P15) while lower results on others (e.g., P1). This is due to the disagreement on the location of the reference points for some cases by the experts.

The instant model currently entails user interaction to select the regions of interest shown in FIG. 1A, though automation of the process is contemplated herein as well and will become clearer as this specification continues. In addition, the 2D dynamic MRI images of 25 patients that were approved by IRB (IRB Study # Pro00007792) were used.

In conclusion, a methodology was presented herein to semi-automatically identify the reference points for evaluation of POP using MRI. The points located on the pubic bone were identified by segmenting the pubic bone and then identifying its reference points. The segmentation of bones on MRI is a challenging task due to weak boundaries and image inhomogeneity. To overcome this problem, a multi-stage segmentation mechanism using texture-based classification, leak detection, and prior shape information is presented. The reference points of the pubic bone were identified using morphological skeleton operation whereas the points located on the vertebra were identified by intersecting point detection methods. Experiments demonstrate that the presented method provides more accurate and faster segmented regions compared to conventional, commonly used segmentation methods. The point identification process is also accurate, faster and consistent compared with the process of manual point identification by experts. The presented method aims to overcome the current limitations of manually identifying points and measurements on MRI and to enable high throughput image analysis.

Example 1

The objective of this study is to design, test and validate a prediction model using SVMs and new MRI-based features to differentiate patients with and without POP.

The main objective of this study is to build a prediction model using SVMs that analyze clinical and new MRI-based features to improve the diagnosis of POP. The current MRI-based features were extracted using the current inventors' previously developed automated pelvic floor measurement model [48, 55]. The significant features, both clinical and MRI-based, were selected using correlation analysis with 95% significance level. The presented prediction model will allow the use of imaging technology to predict the development of POP in predisposed patients, and possibly lead to the development of preventive strategies. Additionally, it is expected that this quantitative prediction model will contribute to a more accurate diagnosis of POP.

I. Materials and Methods

This retrospective study used data from 207 women with different types and stages of prolapse. The demographic information, clinical history, and dynamic MRI data were obtained from the database. New MRI measurements were extracted and analyzed based on these reference lines: true conjugate line (TCL), obstetric conjugate line (OCL), and diagonal conjugate line (DCL). A prediction model using SVM was built and tested to classify cases into prolapse and no prolapse.

A. Data Acquisition

This retrospective study used the data of 207 women with different types and stages of POP from the database of the University of South Florida Division of Female Pelvic Medicine and Reconstructive Surgery within the Department of Obstetrics and Gynecology. The Institutional Review Board at the University of South Florida considered the study exempt. The data collected from the database for each patient includes demographic information, clinical history, POP-Q outcomes, and dynamic MRI-based features (see Table VII). Each patient had been assigned to particular types of prolapse (anterior, apical, and posterior), and their corresponding stage of prolapse (stage 0 through stage 4) using the POP-Q system. This study focuses on a two-class prediction model where prolapse cases were defined as those with stage 2, 3, or 4, whereas controls were defined as those with stage 0 or 1. It was ensured that only patients with complete data were selected for this study.

TABLE VII

Clinical and MRI-based features and sub-features.

| Clinical features: | Clinical sub-features | Feature # |
| --- | --- | --- |
| Age | Age <35 | 1 |
| | 35 ≤ Age < 45 | 2 |
| | 45 ≤ Age < 55 | 3 |
| | 55 ≤ Age < 65 | 4 |
| | 65 ≤ Age < 75 | 5 |
| | 75≤ Age | 6 |
| BMI (kg/m$^2$) | BMI <20 | 7 |
| | 20 ≤ BMI < 25 | 8 |
| | 25 ≤ BMI < 30 | 9 |
| | 30 ≤ BMI < 35 | 10 |
| | 35 ≤ BMI < 40 | 11 |
| | 40≤ BMI | 12 |
| Parity | 0 | 13 |
| | 1 | 14 |
| | 2 | 15 |
| | 3 | 16 |
| | 4 | 17 |
| | 5 | 18 |
| | 5≤ | 19 |
| Gravida | 0 | 20 |
| | 1 | 21 |
| | 2 | 22 |
| | 3 | 23 |

TABLE VII-continued

Clinical and MRI-based features and sub-features.

|  |  |  |
|---|---|---|
|  | 4 | 24 |
|  | 5≤ | 25 |
| Vaginal delivery | 0 | 26 |
|  | 1 | 27 |
|  | 2 | 28 |
|  | 3 | 29 |
|  | 4 | 30 |
|  | 5 | 31 |
|  | 6≤ | 32 |
| Caesarean delivery | 0 | 33 |
|  | 1 | 34 |
|  | 2 | 35 |
|  | 3≤ | 36 |
| Ethnicity | Caucasian | 37 |
|  | African American | 38 |
|  | Hispanic | 39 |
| Hysterectomy | Abdominal Incision | 40 |
|  | Laparoscopic | 41 |
|  | Vaginal | 42 |
| Uterosacral colpopexy | Abdominal | 43 |
|  | Laparoscopic | 44 |
|  | Vaginal | 45 |
| Sacrospinous ligament fixation | Yes | 46 |
|  | No | 47 |
| Sacrocolpopexy | Yes | 48 |
|  | No | 49 |
| Cystocele (anterior) repair | Traditional | 50 |
|  | Graft augmentation | 51 |
| Rectocele (posterior) repair | Traditional | 52 |
|  | Graft augmentation | 53 |
| Incontinence surgery | Burch/MMK | 54 |
| MRI-based features: | MRI-based sub-features | Feature # |
| H-Line | Anterior | 55 |
|  | Apical | 56 |
|  | Posterior | 57 |
| Distance ratio | PCL/MPL | 58 |
|  | TCL/MPL | 59 |
|  | OCL/MPL | 60 |
|  | DCL/MPL | 61 |
| Angle | between TCL and MPL | 62 |
|  | between DCL and PCL | 63 |

The characteristics of the studied group are shown in Table VIII. Variables include age, body mass index, parity, gravidity, number of vaginal deliveries, and number of caesarean deliveries. As shown in the table, 28% of the patients were between 56-65 years old, 25% of them were between 66-75 years old, and 23% of patients were between 46-55 years old. Only 2% of the patients were younger than 35 years old.

Table IX shows the distribution of prolapse cases with their corresponding stages for the studied group. For anterior and posterior prolapse, the majority of the patients are in the stages 2 and 3. On the other hand, the majority of the patients with apical prolapse are in the stages 0 and 1.

TABLE IX

Distribution of prolapse cases with corresponding stages for the studied group.

| Stage | Anterior Prolapse | Apical Prolapse | Posterior Prolapse |
|---|---|---|---|
| 0 | 2% (4) | 10% (20) | 2% (4) |
| 1 | 26% (53) | 63% (131) | 26% (53) |
| 2 | 24% (48) | 6% (11) | 38% (80) |
| 3 | 39% (83) | 12% (22) | 27% (56) |
| 4 | 9% (19) | 9% (19) | 7% (14) |
| TOTAL | 100% (207) | 100% (207) | 100% (207) |

The dynamic MRI data was de-identified and stored on a secure research computer for analysis. MR imaging was performed on a 3-Tesla GE system (General Electric Company, GE Healthcare, Buckinghamshire, UK) using an 8-channel torso phased-array coil with the patient in a modified dorsal lithotomy position. Prior to imaging, 60 ml of ultrasound gel was placed in the rectum for improved visualization. Dynamic imaging was performed in a multi-phase, single-slice sequence. The images were acquired in the midsagittal plane for 23-27 seconds, using a T2-weighted single-shot fast-spin echo sequence. Patients were coached, prior to imaging, on performance of an adequate valsalva maneuver. The image data has been preprocessed and de-identified.

After acquiring the images, new and commonly used MRI-based image features were extracted from the images using the previously developed automated pelvic floor measurement model [7, 48, 55]. Previous MRI studies have mostly used PCL and MPL lines for the radiological assessment of POP. In this study, additional reference lines and angles were introduced and analyzed: TCL, OCL, and DCL, angle between diagonal conjugate line and PCL, and angle between obstetric conjugate line and MPL as shown in FIG. 1B. These reference lines may provide additional insight on the correlation between MRI-based measurements and clinical outcomes due to differences in pelvic configuration.

The following sections provide the description for extracting the MRI-based features using the current model, and for building the prediction model with clinical and MRI-based features for POP diagnosis.

TABLE VIII

Patient characteristics.

|  | Control (Stages 0-1) | | | Prolapse (Stages 2-3-4) | | |
|---|---|---|---|---|---|---|
| Variables | Anterior (n = 57) | Apical (n = 151) | Posterior (n = 58) | Anterior (n = 150) | Apical (n = 56) | Posterior (n = 149) |
| Age | 57.5 ± 11.3 | 57.1 ± 12.2 | 58.9 ± 12.0 | 58.2 ± 11.9 | 60.6 ± 10.0 | 57.7 ± 11.7 |
| Body mass index (kg/m$^2$) | 27.5 ± 6.1 | 27.8 ± 5.7 | 26.0 ± 6.2 | 27.4 ± 5.6 | 26.6 ± 5.8 | 28.0 ± 5.5 |
| Parity | 2.5 ± 1.3 | 2.6 ± 1.3 | 2.5 ± 1.2 | 2.6 ± 1.3 | 2.6 ± 1.4 | 2.7 ± 1.4 |
| Gravidity | 3.3 ± 1.8 | 3.2 ± 1.7 | 3.1 ± 1.8 | 3.2 ± 1.7 | 3.3 ± 1.8 | 3.3 ± 1.7 |
| Number of vaginal deliveries | 2.4 ± 1.4 | 2.5 ± 1.3 | 2.3 ± 1.2 | 2.5 ± 1.3 | 2.6 ± 1.4 | 2.6 ± 1.4 |
| Number of caesarean deliveries | 0.2 ± 0.5 | 0.1 ± 0.5 | 0.2 ± 0.5 | 0.1 ± 0.4 | 0.0 ± 0.2 | 0.1 ± 0.4 |

B. Methods a. Automatic Extraction of MRI-Based Features

Prior to MRI-based feature extraction, MR images were pre-processed to reduce image noise, and to improve image contrast. Image noise reduction was performed by applying a convolution operation with a Gaussian smoothing kernel. Then, contrast stretching (image normalization) was performed to provide better intensity spread of pixels and to adjust de-noised images to gain better contrast. Finally, the images were calibrated to enable the gathering of real measurement values.

The proposed reference lines and angles were automatically extracted from MRI using the previously developed pelvic floor measurement model [7, 48, 55]. The model automatically identifies multiple bone structures on MRI and then extracts MRI-based features (lines, measurements, and angles).

b. Prediction Model

A prediction model was built to analyze clinical and MRI-based features to differentiate patients with and without prolapse (anterior, apical, or posterior). The model is a two-class prediction model trained using SVM and incorporating features selected by correlation analysis at 95% significance level. SVM was selected as it has shown to achieve the highest classification accuracy for medical diagnosis compared to conventional classification techniques [56].

The significant features, both clinical and MRI based were selected using correlation analysis. Pearson's correlation coefficient is used to measure the linear association between variables and is defined as follows:

$$\text{corr}(x, y) = \frac{\text{covariance}(x, y)}{\text{standart deviation}(x) * \text{standart deviation}(y)} = \frac{S_{xy}}{S_x S_y} \quad (8)$$

After selecting the best descriptive set of features, a classifier was built for each type of prolapse using SVM. The classification involves two steps: construction of the classifier and prediction. The dataset was divided into a training dataset and testing dataset for the prediction model. In the first step, a classifier structure is constructed based on the training data set using SVMs. SVMs were trained using the "kernel trick", which allows the algorithm to fit the maximum margin hyperplane in a transformed feature space to provide for a non-linear decision surface. The training vectors $x_i$, i=1, 2, ..., L are nonlinearly mapped onto a high-dimensional feature space by $\Phi: \mathbb{R}^M \mapsto \mathcal{F}$ and then a linear separation is attempted in $\mathcal{F}$. If $\mathcal{F}$ is a Hilbert space, K is a kernel function in the original space $\mathbb{R}^M$ that describes the inner product in $\mathcal{F}$.

$$\Phi(u) \cdot \Phi(v) = K(u, v) = (u \cdot v + 1)^2 \quad (9)$$

where K(u,v) should satisfy Mercer's condition that ensures that the kernel function can always be expressed as the dot product between two input vectors in high dimensional space. This transformed space of the SVM kernels is called a reproducing kernel Hilbert space. The RBF kernel was employed in the training process to construct nonlinear SVMs and is described as follows:

$$K(u, v) = \exp(-\gamma \|u - v\|^2) \quad (10)$$

There are two parameters for an RBF kernel that need to be determined: C representing the penalty parameter and $\gamma$ representing the RBF sigma parameter. 10-fold cross validation was used in this study to identify the best (C,$\gamma$) so that the classifier can accurately predict unknown data. After the cases were trained using the selected features, the second step of the prediction model was to apply the model to test cases in the testing dataset using the built SVM classifier. The outcome at the end of this process was a set of two groups of cases that are automatically classified as either prolapse group or control group.

II. Results

Generally, it was found that the prediction model can accurately classify cases of anterior prolapse with very high accuracy (>0.90), and of apical and posterior prolapse with good accuracy (0.80-0.90). Two newly proposed MRI-based features were found to be significant in the prediction of anterior and posterior prolapse. For posterior prolapse, the prediction accuracy increased from 47% to 80% by considering the newly proposed MRI-based features.

More specifically, a total of forty (63) clinical and MRI-based features were collected and analyzed in this study. For each type of POP, the significant features were identified using correlation coefficient (r) at 95% significant level. As shown in Tables X-XII, the set of significant features vary based on the type of POP. For instance, body mass index<20 (r=−0.1879; p=0.0067) was found to be significant for posterior prolapse but not for anterior or apical prolapse. Ethnicity (Caucasian) was found to have an impact on apical prolapse but not on anterior or posterior prolapse (r=−0.2002; p=0.0038). As shown in the tables, the current MRI-based features were also found to be significant in the prediction of the different types of prolapse. H-Line anterior (r=0.4339; p=0.0003), H-Line apical (r=0.3489; p=0.0021), and the angle between TCL and MPL (r=0.1337; p=0.0154) have an impact in the assessment of anterior prolapse whereas H-Line posterior (r=0.2355; p=0.006) and the angle between DCL and PCL (r=0.1239; p=0.014) were found to impact the prediction of posterior prolapse. Only H-Line anterior (r=0.2654; p=0.0011) and H-Line apical (r=0.3775; p=0.0002) were found to be significant MRI-based features in the assessment of apical prolapse.

TABLE X

Significant features for anterior prolapse.

| | Correlation coefficient (r) | p value |
|---|---|---|
| Clinical features: | | |
| # of Vaginal delivery = 2 | 0.1606 | 0.0208 |
| # of Cesarean delivery = 2 | −0.1492 | 0.0320 |
| Hysterectomy-Abdominal incision | −0.1995 | 0.0040 |
| Hysterectomy-Laparoscopic | −0.1432 | 0.0395 |
| Hysterectomy-Vaginal | −0.1730 | 0.0127 |
| Sacrocolpopexy | −0.2692 | 0.0087 |
| MRI-based features: | | |
| H-Line Anterior | 0.4339 | 0.0003 |
| H-Line Apical | 0.3489 | 0.0021 |
| Angle between TCL and MPL | 0.1337 | 0.0154 |

TABLE XI

Significant features for apical prolapse.

| | Correlation coefficient (r) | p value |
|---|---|---|
| Clinical features: | | |
| Ethnicity-Caucasian | −0.2002 | 0.0038 |
| Hysterectomy-Abdominal incision | −0.2155 | 0.0018 |

TABLE XI-continued

Significant features for apical prolapse.

| | Correlation coefficient (r) | p value |
|---|---|---|
| Rectocele (posterior) repair-Graft augmentation | 0.1515 | 0.0293 |
| MRI-based features: | | |
| H-Line Anterior | 0.2654 | 0.0011 |
| H-Line Apical | 0.3775 | 0.0002 |

TABLE XII

Significant features for posterior prolapse.

| | Correlation coefficient (r) | p value |
|---|---|---|
| Clinical features: | | |
| 35 <= Age < 45 | 0.1715 | 0.0135 |
| BMI <20 | −0.1879 | 0.0067 |
| Sacrocolpopexy | −0.1539 | 0.0268 |
| Rectocele (posterior) repair-Traditional | −0.1510 | 0.0298 |
| MRI-based features: | | |
| H-Line Posterior | 0.2355 | 0.006 |
| Angle between DCL and PCL | 0.1239 | 0.014 |

Table XIII shows the distribution of cases for the training and testing datasets for each type of prolapse. Then, Table XIV shows the distribution of prolapse stages within the testing and training datasets per type of prolapse. The prediction model was trained using SVM. For anterior prolapse, the model was trained using the data from 138 cases (100 prolapse cases, 38 controls). After training the classifier based on the selected clinical and MRI-based features, the testing process was performed on 69 cases (50 prolapse cases, 19 controls). Similarly, the prediction model was trained for apical prolapse with 138 cases (37 prolapse cases, 101 controls) and the testing process was performed with 69 cases (19 prolapse cases, 50 controls). Finally, for posterior prolapse, the model was trained with 136 cases (98 prolapse cases, 38 controls) and tested on 71 cases (51 prolapse cases, 20 controls).

TABLE XIII

Assignment of cases for training and testing the prediction model.

| Group | Training Dataset | Testing Dataset | TOTAL |
|---|---|---|---|
| Prolapse | | | |
| Anterior | 100 | 50 | 150 |
| Apical | 37 | 19 | 56 |
| Posterior | 98 | 51 | 149 |
| Control | | | |
| Anterior | 38 | 19 | 57 |
| Apical | 101 | 50 | 151 |
| Posterior | 38 | 20 | 58 |

TABLE XIV

Distribution of prolapse stages within the testing and training datasets.

| | Training Dataset | | | | | Testing Dataset | | | | | |
|---|---|---|---|---|---|---|---|---|---|---|---|
| | CONTROL | PROLAPSE | | | | CONTROL | PROLAPSE | | | | |
| Type of prolapse | Stage 0 | Stage 1 | Stage 2 | Stage 3 | Stage 4 | Stage 0 | Stage 1 | Stage 2 | Stage 3 | Stage 4 | TOTAL |
| Anterior | 2 | 36 | 32 | 56 | 12 | 2 | 17 | 16 | 28 | 6 | 207 |
| Apical | 13 | 88 | 9 | 16 | 12 | 7 | 43 | 4 | 9 | 6 | 207 |
| Posterior | 2 | 36 | 52 | 36 | 10 | 2 | 18 | 28 | 18 | 5 | 207 |

The current prediction model was validated using the correct rate, which is the percentage of cases correctly classified. Table XV provides the accuracy comparison between the prediction model using different sets of features: (1) only clinical features, (2) only MRI-based features, and (3) both clinical and MRI-based features. As can be seen in the table, considering both clinical and the newly proposed MRI-based features increases the prediction accuracy of all types of prolapse. This improvement is especially noticeable on posterior prolapse where the consideration of both types of features increased the correct rate from about 47% to about 80%. The significant clinical features for posterior prolapse were found to be: age (35<=Age<45) (r=0.1715; p=0.0135), body mass index <20 kg/m² (r=−0.1879; p=0.0067), previous rectocele (posterior) repair with traditional method (r=−0.1510; p=0.0298), and previous sacrocolpopexy (r=−0.1539; p=0.0268). The significant MRI-based features for posterior prolapse are H-Line (r=0.2654; p=0.00114) and the angle between DCL and PCL (r=0.1239; p=0.014).

TABLE XV

Accuracy of the current prediction model for different types of prolapse and different types of features.

| | Correct rate (ONLY clinical features) | Correct rate (ONLY MRI-based features) | Correct rate (BOTH clinical and MRI-based features) |
|---|---|---|---|
| Anterior | 82 | 56 | 91 |
| Apical | 83 | 53 | 89 |
| Posterior | 47 | 52 | 80 |

For anterior prolapse, the model correctly predicted 91% of the cases using clinical and MRI-based features. Clinical features found to be significant include: # of Vaginal delivery=2 (r=0.1606; p=0.0208), # of Cesarean delivery=2 (r=−0.1492; p=0.0320), Hysterectomy-Abdominal incision (r=−0.1995; p=0.0040), Hysterectomy-Laparoscopic (r=−0.1432; p=0.0395), Hysterectomy-Vaginal (r=−0.1730; p=0.0127), Sacrocolpopexy (r=−0.2692; p=0.0087) whereas MRI-based features include H-Line anterior (r=0.4339; p=0.0003), H-Line apical (r=0.3489; p=0.0021), and the angle between TCL and MPL (r=0.1337; p=0.0154). Finally, for apical prolapse, 89% of the cases were correctly predicted using both clinical and MRI-based features. Significant clinical features for apical prolapse were found to be Ethnicity-Caucasian (r=−0.2002; p=0.0038), Hysterectomy-Abdominal incision (r=−0.2155; p=0.0018), and previous Rectocele (posterior) repair using graft augmentation (r=0.1515; p=0.0293). H-Line anterior (r=0.2654; p=0.0011) and H-Line apical (r=0.3775; p=0.0002) were found to be significant MRI-based features for apical prolapse. Results show that the presented prediction model can predict cases with anterior prolapse with very high accuracy (>0.90), and apical and posterior prolapse with good accuracy (0.80-0.90).

III. Discussion

This study was designed to test a prediction model using SVM and new MRI-based features to differentiate patients with and without POP. Results show that the presented prediction model is able to accurately classify the testing cases into prolapse or control groups. Prediction accuracies for anterior and apical prolapse are higher than for posterior prolapse since the correlation between features and POP-Q outcomes is lower for posterior prolapse. Analysis showed that the newly proposed MRI-based features have a significant impact in the prediction of prolapse cases, particularly for posterior prolapse, which has demonstrated the least correlation with MRI findings in previous studies. These features are the angle between TCL and MPL for predicting anterior prolapse, and the angle between DCL and PCL for predicting posterior prolapse.

Previous studies have shown that the use of the PCL as a reference line on MRI can help in assessing the clinical stages of POP for the anterior and the apical compartment [57, 58]. Diagnosing posterior compartment prolapse has been more challenging. It has been reported that only 51% of rectocele were correctly identified with physical examination compared to imaging studies using cystoproctography [59]. Fauconnier et al. compared clinical measurement points with MRI measurements, and found a good correlation in the anterior and apical compartment, but found no correlation for the posterior compartment [60]. Broekhuis et al. showed high agreement between clinical assessment and dynamic MRI for the anterior and apical compartment but low agreement for the posterior compartment. Therefore, posterior prolapse remains the most difficult type of prolapse to diagnose [8]. Pannu et al. [61] found a relationship between MRI and clinical measurements in identifying POP by using both PCL and MPL in the anterior compartment. The authors found no significant difference in agreement using the MPL or PCL implying that either line can be used on MRI. Cortes et al. [62] performed a correlation analysis between clinical examination and MRI data for vaginal apex prolapse using MPL. They found poor correlation between clinical examination and MRI, and suggested a complementary diagnostic tool to identify complex vaginal apex prolapse. Lienemann et al. [57] investigated which reference lines on functional cine-magnetic resonance imaging correlated best with the clinical diagnosis, which led to the conclusion that POP descent cannot be described using only one reference line and agreement has not been presented.

Robinson et al. [63] demonstrated a prediction model for POP using artificial neural network (ANN) and clinical data only. It was found that 20 variables made the largest contributions to the model such as age, gravidity, parity, and the number of vaginal deliveries. In the study, only clinical data was used and no image data was used.

One of the strengths of this study is the large number of cases in the studied group. A total of 207 women with different types and stages of POP were analyzed in this study and their MRI-based features were extracted automatically using the previously developed pelvic floor measurement model. Using a large number of cases for training the model provides a more powerful prediction model. Another strength of the study is that these cases were obtained from a previously selected dataset so there was no bias on the selection of the studied group. Finally, the presented prediction model proposes and analyzes new MRI-based features. Previous imaging studies have investigated the correlation between clinical features and MRI-based features from commonly used reference lines such as PCL and MPL. These studies found a poor correlation for posterior prolapse. The new MRI-based features proposed and analyzed in this study increased the prediction accuracy of posterior prolapse to 80% compared with using clinical features only (47%). To further increase the prediction accuracy for posterior prolapse, additional image features might need to be analyzed.

The SVM-based prediction model was designed for two-class prediction (prolapse or no prolapse). This was necessary due to the limited number of MR images available with certain stages of prolapse, therefore necessitating a binomial evaluation of the data. In conclusion, the presented prediction model using SVM can correctly classify prolapse cases using clinical and new MRI-based features. The model identified two new MRI-based features that are significant in the prediction of POP: the angle between TCL and MPL for anterior prolapse, and the angle between DCL and PCL for posterior prolapse. The inclusion of these new MRI-based features increased the overall prediction accuracy for prolapse, particularly for posterior prolapse.

In this study, a prediction model that fuses clinical and new MRI-based features was presented to improve the diagnosis of POP. The prediction model uses SVMs and selects significant features using correlation analysis at 95% significant level. Results demonstrate that the current prediction model using both clinical and new MRI-based features achieves higher classification accuracy compared to using only clinical features. Analysis showed that two newly proposed MRI-based features: the angle between TCL and MPL, and the angle between DCL and PCL have a significant impact in the prediction of anterior and posterior prolapse, respectively. For posterior prolapse, the consideration of the new MRI-based features significantly increased the prediction accuracy from 47% to 80%.

Example 2

A fully automated localization system and methodology is presented herein for automatically locating the bounding boxes of multiple pelvic bone structures on MRI using SVM-based classification and non-linear regression model with global and local information. The model identifies the location of the pelvic bone structures by establishing the association between their relative locations and using local information such as texture features. Results show that the current methodology is able to locate the bone structures of interest accurately.

More specifically, the methodology described herein first identifies pelvic organs using k-means clustering and morphological opening operations. Then, it uses the spatial relationship between the organs and bone structures to estimate the locations of the structures. The pubic bone is located using the relative location between bones and organs, and texture information. Then, a non-linear regression model is used to predict the location of other bone structures whose local information is insufficient, such as sacral promontory and coccyx. The main contribution of this methodology is a new parameterization through non-linear regression approach for the multiple bone localization problem on MRI.

I. Multiple Bone Localization

As shown in FIG. 1A, three ROIs need to be located automatically that correspond to the pubic bone, sacral promontory, and coccyx, respectively. However, bones are not easily differentiable from soft tissues on MRI as their pixel intensities tend to be very similar. This is particularly true for bones located on the vertebra such as sacral promontory and coccyx. On the other hand, both the bladder and the rectum are visible as retrograde bladder/ureteral dye is injected during image capture to enhance visualization. Therefore, the regions for both the bladder and the rectum have high intensity values on the MR images and can be used as contextual information to automatically locate the pelvic floor structures of interest. Based on these observations, the current methodology is designed to localize the pubic bone first using both global and local information, and then use global information to localize the sacral promontory and coccyx.

Figure 7:
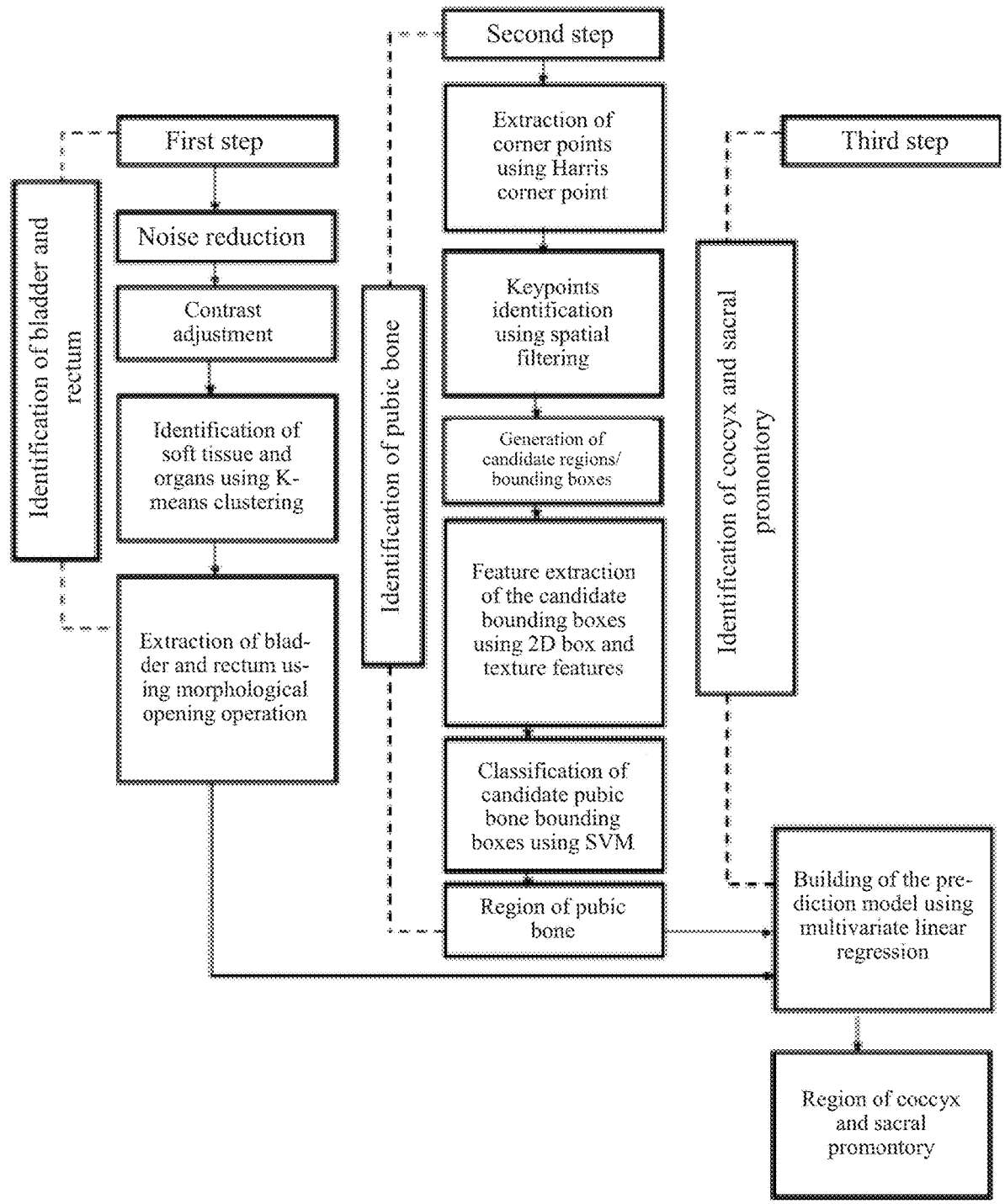
FIG. 7 is an overview of current methodology according to an embodiment of the current invention.

The current methodology includes three main phases: identification of bladder and rectum, identification of pubic bone region, and identification of coccyx and sacral promontory regions (see FIG. 7). The first phase starts with noise reduction and contrast adjustment of the images. Then, the bladder and rectum are identified using bisecting K-means clustering using pixel intensities and morphological opening operation. In the second phase, the pubic bone region is localized based on "keypoints", which are corner points on the input image that satisfy certain intensity and location constraints. Based on the identified keypoints, candidate bounding boxes of the pubic bone can be determined. The best bounding box that describes the pubic area is selected using SVMs with 2D box features. In the third phase, the coccyx and sacral promontory regions are localized using the location of the bladder, rectum and pubic bone via a non-linear regression model.

A. Dataset Description

A representative set of 207 dynamic MRI were used in this study. MR images were obtained from a 3-Tesla GE system (General Electric Company, GE Healthcare, UK) using an 8-channel torso phased-array coil with the patient in a modified dorsal lithotomy position (patient laying in the supine position with their knees slightly elevated and abducted under a support). Dynamic MRI of the pelvis is performed using a T2-weighted single-shot turbo spin-echo (SSH-TSE) sequence in the midsagittal plane for 23-27 seconds with a temporal resolution of 2 s (FOV 300×300 mm$^2$, slice thickness 3 mm, TR/TE 2,000/75 ms, 20 image sequences, in-plane resolution of 1.6×1.6 mm$^2$). Subjects were coached, prior to imaging, on performance of an adequate valsalva maneuver (straining maneuver) to observe the movement of the pelvic organs from rest to maximum strain. The image data has been preprocessed and de-identified.

B. Identification of Bladder and Rectum

The first phase of the current methodology is to perform noise reduction by applying a 3×3 Gaussian kernel (Gaussian smoothing with σ=0.8) due to its computational efficiency. After noise reduction, contrast adjustment is performed to improve the contrast in the images by stretching the range of intensity values. Minimum and maximum values used for normalization are 0 and 255, respectively.

Given the clear visibility of the bladder and the rectum on dynamic MRI due to ureteral dye use, these two organs can be automatically identified to be used as contextual information for the localization of the bone structures. A "bisecting K-means" algorithm was used to identify regions on the image and to overcome the initialization susceptibility of the basic K-means clustering algorithm. The idea is to obtain K clusters by first splitting the set of all points into two clusters. Then one of these clusters is selected for splitting, and the process continues until k clusters are generated. In the study, the value of k is 4 because the region of the pelvic floor is divided into four (4) subregions representing the bone, cartilage, soft tissue and organ, and background.

Figure 8A:
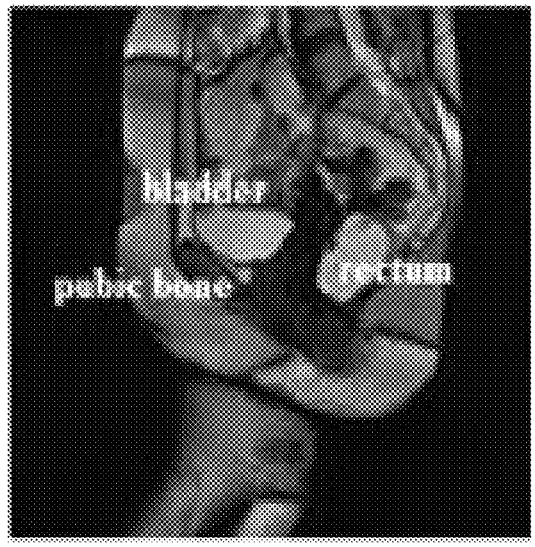
FIG. 8A is an input image for bladder and rectum localization.
Figure 8B:
FIG. 8B illustrates bladder and rectum localization with clustering with k=4.
Figure 8C:
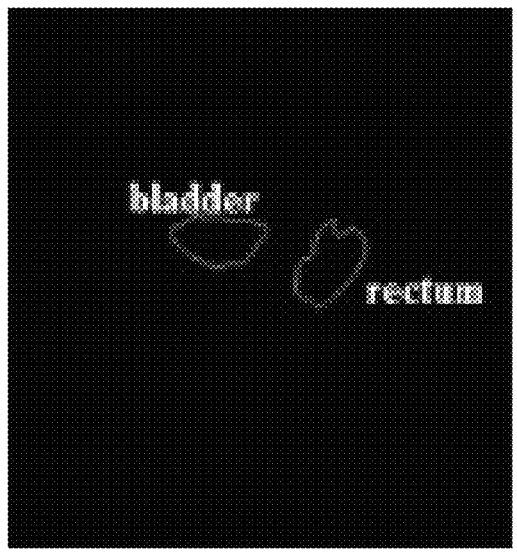
FIG. 8C depicts identified regions for bladder and rectum using size, homogeneity, and location constraints.

After identifying the four (4) types of regions, the regions with the highest intensity are selected to locate the bladder and rectum regions. However, many regions with similar intensities to the bladder and rectum may be identified as shown in FIG. 8B. To separate the bladder and rectum, size, homogeneity, and location constraints were incorporated. For size constraint, connected regions that have less than a specified number of pixels were removed using morphological opening operations. For homogeneity, it was observed that the bladder and rectum regions on MRI are homogeneous regions without internal holes. Therefore, the Euler number, which is a topological descriptor, was used to determine the number of holes inside the regions and to eliminate those regions with internal holes. Finally, as location constraint, the location of the bladder and rectum normally appear close to the center of the image so the search of these two organs was limited to the center of the image. The results of this process are shown in FIG. 8C.

The mathematical description of this filtering operation to find the desired regions H (bladder and rectum) is shown below. $R_l$ corresponds to the set of regions obtained after clustering.

$$H = \{s_{min} < S_{R_l} < s_{max}$$

$$\phi_{R_l} = 1$$

$$d_{Rdi\ l} < r \forall R_l \in R\} \quad (11)$$

where $S_{R_l}$ denotes the size of the $l^{th}$ region in set R, which was obtained through bisecting K-means clustering, $s_{min}$ and $s_{max}$ are the minimum and maximum region sizes, respectively. $\phi_{R_l}$ is the specified Euler number which is 1. $d_{R_l}$ denotes the distance between the centroid of the $l^{th}$ region and the midpoint of the image, and r is the specified distance.

C. Identification of Pubic Bone Region a. Keypoints Extraction

After the locations for the bladder and rectum have been identified, the next phase is to identify the location of the pubic bone. This is achieved through the identification of keypoints on the image that satisfy specific location and intensity constraints. The use of corner points was selected instead of pixels because corner points can be extracted without any user input and it is computational efficient.

Corner points are identified using the Harris corner detector [32] with sensitivity factor of 0.04. These corner points are determined by evaluating the autocorrelation function of the input image which measures the local changes of the patches moved by a small amount in a different direction. Corner point extraction is followed by spatial filtering to eliminate the number of corner points that are outside of the vicinity of the bladder. The following equations provide the mathematical framework of the spatial filtering operation. Set C corresponds to the set of locations obtained after an initial selection of corner points.

$$C = (p(x,y) \in P: T_1 < I(xy) < T_2$$

$$d_1 < p(x) - c(x) < d_2$$

$$c(y) < p(y) < d_3 \text{ and } \forall p \in P\} \quad (12)$$

where p(xy) denotes the interest point location, P is the set of points obtained by the Harris corner detector, I(xy) denotes the intensity level at p(xy), $T_1$ is the threshold for minimum pixel intensity, $T_2$ is the threshold for maximum pixel intensity, and d and $d_2$ denote the minimum and maximum distances between the key points and the centroid of the bladder on the x direction, respectively. $d_3$ is the maximum distance between the key points and the centroid of the bladder on the y direction, where c(x) and c(y) denote the centroids of the regions on the x and y direction, respectively. These distances are determined based on the relative positions between anatomical structures on the body from the training image dataset. The constraints ensure that corner points that are below and to the left of the bladder and within a specific distance and intensity range are retained. For instance, the mean intensity value of pixels located on the pubic bone has been defined as 33±10.4 using histogram analysis over the training image dataset. Hence, corner points with intensity levels between 10 and 60 can be considered as potential keypoints corresponding to the pubic bone.

b. Generation of Candidate Bounding Boxes

Figure 9A:
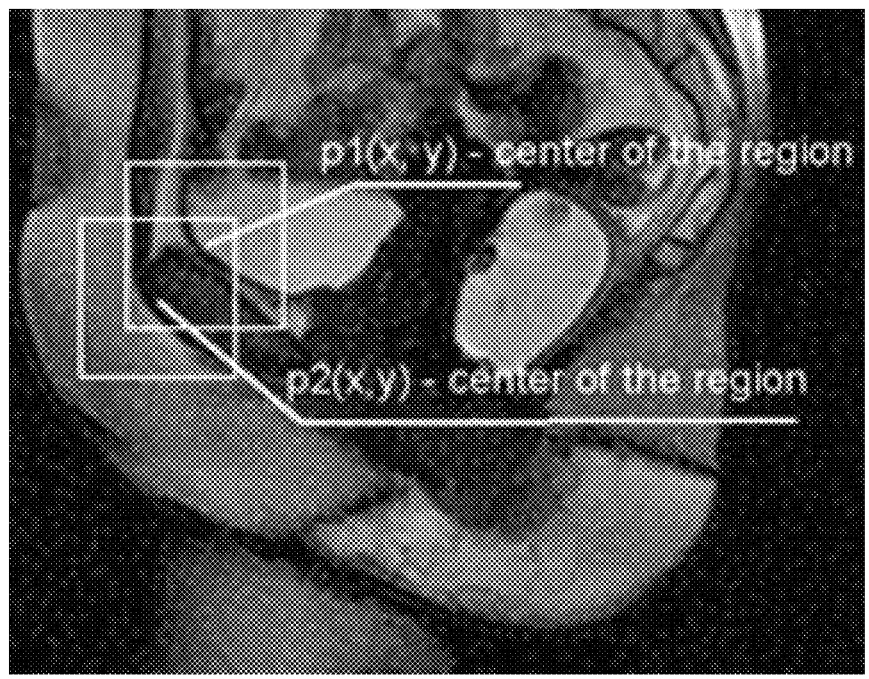
FIG. 9A shows candidate region generation with keypoints used as centroids of candidate regions.
Figure 9B:
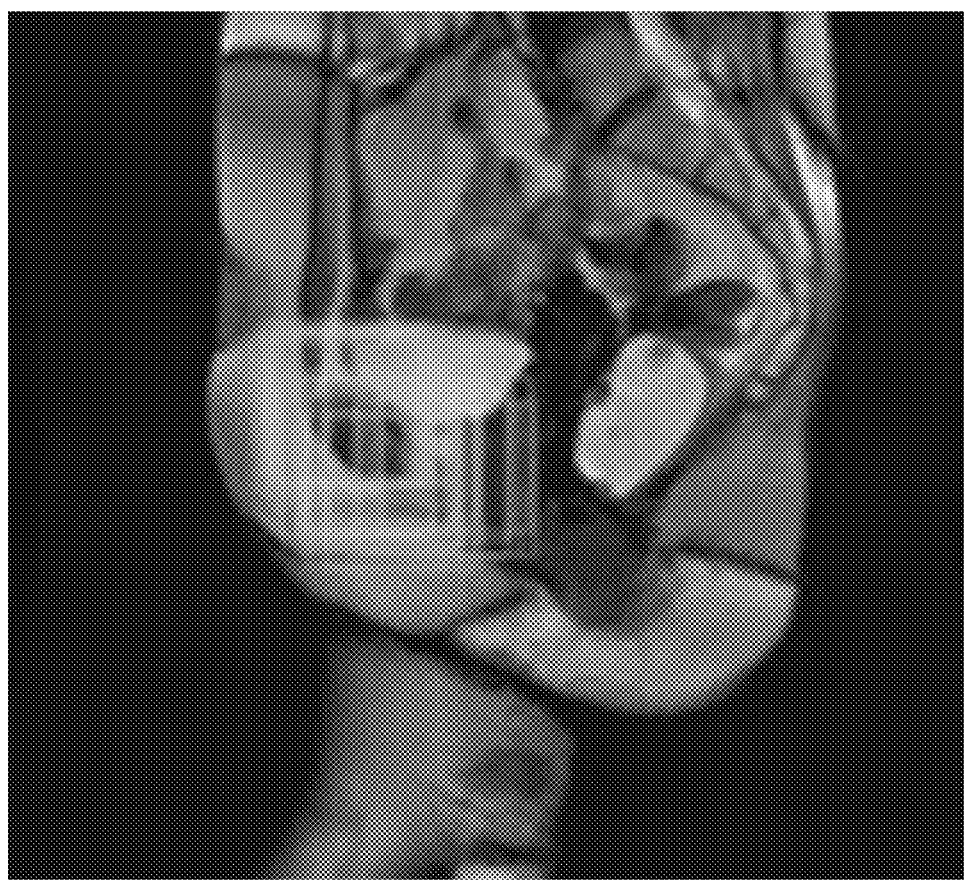
FIG. 9B shows candidate region generation with candidate regions of pubic bone.

After spatial filtering, potential pubic bone regions are generated as seen in FIGS. 9A-9B. These bounding boxes are centered at the keypoints, and the size is set to a value defined by analyzing the training image dataset. Principal component analysis (PCA) is applied to the manually segmented pubic bone regions in the training image dataset to find the mean shape and the shape variation models of the pubic bone. This is used to determine the size of the bounding boxes to enclose the pubic bone. Each of these bounding boxes represents a potential bounding box for the pubic bone.

However, some of these bounding boxes do not completely enclose the pubic bone as the keypoints may fall near the boundaries of the bone. For this reason, the bounding boxes that completely enclose the pubic bone need to be identified. To do this, it is proposed to analyze each bounding box based on Haar-like [69] and texture features. Haar-like features provide the average intensity difference between two displaced boxes (horizontal, vertical, and central differences). Texture features have shown to enable more reliable results on MRI by providing the relative position information of any two pixels with respect to each other [7], [48]. We used a total of 303 features: 297 generated by Haar-like features and six texture features. The texture features used in this study are average gray level, average contrast, smoothness, skewness, uniformity, and entropy.

c. Feature Extraction of Candidate Regions

The selected features need to be robust to represent changes and imaging conditions on each candidate region/bounding box. The candidate regions are evaluated based on 2D box features and texture features. 2D box features provide the average intensity difference between two displaced boxes. Texture features have shown to enable more reliable results on MRI by providing the relative position information of any two pixels with respect to each other [17, 18]. The selected texture features in this study are average gray level, average contrast, smoothness, skewness, uniformity, and entropy.

d. Classification of Bounding Boxes

The feature set representing the candidate regions/bounding boxes are evaluated using SVMs. SVM has been shown to achieve the highest classification accuracy for medical diagnosis compared to conventional classification techniques [7, 48-50]. The current study includes a two-class problem where candidate bounding boxes are classified into bounding boxes of pubic bone or not. The classification of the candidate regions involves two steps: construction of the classifier and prediction. In the first step, a classifier structure is constructed based on the training data set using SVM. SVM was trained using the radial basis function (RBF) kernel to provide for non-linear decision surface.

There are two parameters in the kernel that need to be determined: C representing the penalty parameter, and γ representing the RBF sigma parameter. A grid search was implemented using 100 runs of tenfold cross validation to identify the best (C,γ) so that the classifier can accurately predict the unknown data. The search range of SVM parameters for cross validation is $C=2^{-5}, 2^{-3}, \ldots 2^{15}$ and $\gamma=2^{-15}, 2^{-13}, \ldots 2^3$. The best values were found to be C=2 and γ=0.000488.

After the bounding boxes are trained according to the features, the built SVM classifier is used to test the images. The anticipated outcome at the end of this process is a set of two groups of bounding boxes that are automatically classified as enclosed pubic bone regions and partially enclosed pubic bone regions.

D. Identification of Coccyx and Sacral Promontory Regions

The locations of the bladder, rectum, and pubic bone are strongly correlated with the locations of the sacral promontory and coccyx. However, the relationship between these organs is complex given the different sizes and locations of the organs. Thus, a non-linear regression model was built to predict the location of the coccyx and sacral promontory regions.

The current non-linear model has been trained through parameterizing the location of the pelvic floor structures with respect to the bladder, rectum and pubic bone locations. For training, the input was considered as $(S_i, P_i)$, where $S_i$ is the input matrix and $P_i$ is the predicted matrix. $S_i$ includes $c_{i1}{}^j(x,y)$, $d_{i1}(x,y)$, and $d_{i2}(x,y)$, where $c_{i1}{}^j(x,y)$ is the location of the centroid of structure j for the $i^{th}$ subject, j corresponds to the regions (bladder, rectum, pubic bone, coccyx and sacral promontory), $d_{i1}(x,y)$ and $d_{i2}(x,y)$ are the relative distances between the centroids of the bladder and rectum to the centroid of the pubic bone, respectively. $P_i$ includes $d_{i3}(x,y)$ and $d_{i4}(x,y)$, where $d_{i3}(x,y)$ and $d_{i4}(x,y)$ are the distances between the centroids of sacral promontory and coccyx to the centroid of the pubic bone, respectively. $P_i$ helps in predicting the sacral promontory and coccyx regions for the testing image dataset.

After parameterization, the next step was to choose the model function to fit the model to the dataset. The selection of the model function may determine the accuracy of the model. The data set has been trained using different non-linear models and the exponential polynomial model has been selected since it provides the minimum distance between the model curve and data points. Another reason for the selection of this model is that the residuals appear randomly distributed across the zero line indicating that the model is a good fit. The goodness of fit has also been measured using quantitative measures such as R squared. The selected model provided the highest R squared among the other models. The selected non-linear model can be expressed as follows:

$$f(V,\beta) = e^{\beta_0 + \beta_1 V_1 + \beta_2 d_1^2 + \beta_3 2^3} \quad (13)$$

Unlike in linear regression, most non-linear regression models require initialization of the parameters ($\beta_0$, $\beta_1$, $\beta_2$, and $\beta_3$). In order to find the initial values, the data set has been transformed and analyzed using linear regression. After selecting the initial values, the parameters are estimated from the dataset by minimizing the distance between the model curve ($f(V,\beta)$) and the data points ($\gamma_i$) using the equation below:

$$\Sigma_{n=1}^{n}[y_i - f(V,\beta)]^2 \quad (14)$$

Once the centroids of the sacral promontory and coccyx are determined, the bounding boxes that enclose these regions are determined based on PCA by generating the mean boxes and box variations of the coccyx and sacral promontory regions. PCA provides fixed size bounding boxes for each region. For instance, the maximum size for the bounding box of the sacral promontory has been defined as [60 px 60 px] based on the training dataset and PCA. For the coccyx, the maximum size for the bounding box was determined to be [30 px 30 px]. These bounding boxes are centered at the centroids of the sacral promontory and coccyx.

II. Results

The current automated bone localization model was evaluated on a wide range of MR images along the mid-sagittal view and at different stages of POP (from stage 0 to stage 4). The validation of the current model was performed on a representative clinical data set of 207 selected dynamic MRI. The methodology was implemented using MATLAB 2012b on a workstation with 3.00-GHz dual processors and 2-GB RAM.

A. Multiple Bone Localization

The regions identified through the current localization method were compared to the regions identified manually by experts. The Euclidean distance between the centers of the predicted and ground truth bounding boxes was used to assess the accuracy of the bone localization approach. In addition, the region overlap between the predicted and ground truth regions was quantified using the DSI, where $$DSI = 2 \cdot \frac{|A_{ref} \cap A|}{|A_{ref}| + |A|} \quad (15)$$

where $A_{ref}$ and $A$ indicate the manual and automatic segmented regions, respectively. Since this bone localization approach depends on the identified bladder and rectum locations, they have also been evaluated independently using center error rate and DSI.

Tenfold cross validation experiments were conducted to evaluate the performance of the current model and two other organ localization models: multiatlas-based model [70] and regression forest [46]. These validation experiments were repeated 100 times for stability. The multiatlas-based localization model was implemented as follows: 100 runs of tenfold cross validation experiments with grid search were conducted to find the optimum similarity index (selected similarity index is 0.0025). Five different average shape atlases were generated using affine-based transformation, intensity-based similarity measure, and genetic algorithm for optimization. These five atlases were generated to represent the five stages of prolapse and to eliminate bias on selecting an atlas during the registration process. For each image of the dataset, each atlas was registered to the image using affine-based registration. The location error of the bounding boxes was calculated based on the ground truth bounding boxes for each atlas. The mean error on lower and upper bounds was computed over the dataset.

For the regression forest model, 100 runs of tenfold cross validation experiments with grid search were conducted to find the best parameters, number of forest size, and tree depth. The best result was obtained with forest size of 9 and tree depth of 6. The node optimization model described in [46] was performed to predict the location of the bounding boxes.

Table VI provides the average center error in millimeter for the regression forest model, the multiatlas-based model, and the current localization model. It can be observed that the current model provides the lowest average center error in the localization of the bladder, rectum, pubic bone, and coccyx regions compared to conventional methods. The average center error for the sacral promontory region by the current model was 0.6-mm higher than the average center error by the regression forest. For all the models and among the bone structures only, the average center error for the pubic bone is the lowest, whereas for the coccyx is the highest. This is due to the low variability in location of the pubic bone compared with the coccyx.

TABLE VI

Average center error (mean ± standard deviation) for structure localization by the current localization model compared to conventional localization models.

| | Center error (mm) | | | |
|---|---|---|---|---|
| | Regression forest | Multiatlas lower bound | Multiatlas upper bound | Current model |
| Bladder | 4.1 ± 1.7 | 20.2 ± 2.8 | 81.1 ± 11.5 | 2.1 ± 0.4 |
| Rectum | 7.6 ± 3.8 | 46.2 ± 7.4 | 85.2 ± 19.6 | 3.2 ± 2.1 |
| Pubic bone | 5.8 ± 1.6 | 11.1 ± 3.9 | 15.6 ± 9.4 | 4.2 ± 1.7 |
| Coccyx | 17.2 ± 5.4 | 20.3 ± 13.9 | 26.3 ± 24.5 | 15.9 ± 2.6 |
| Sacral promontory | 8.6 ± 2.8 | 14.9 ± 6.2 | 17.6 ± 16.8 | 9.2 ± 2.7 |

Figure 10A:
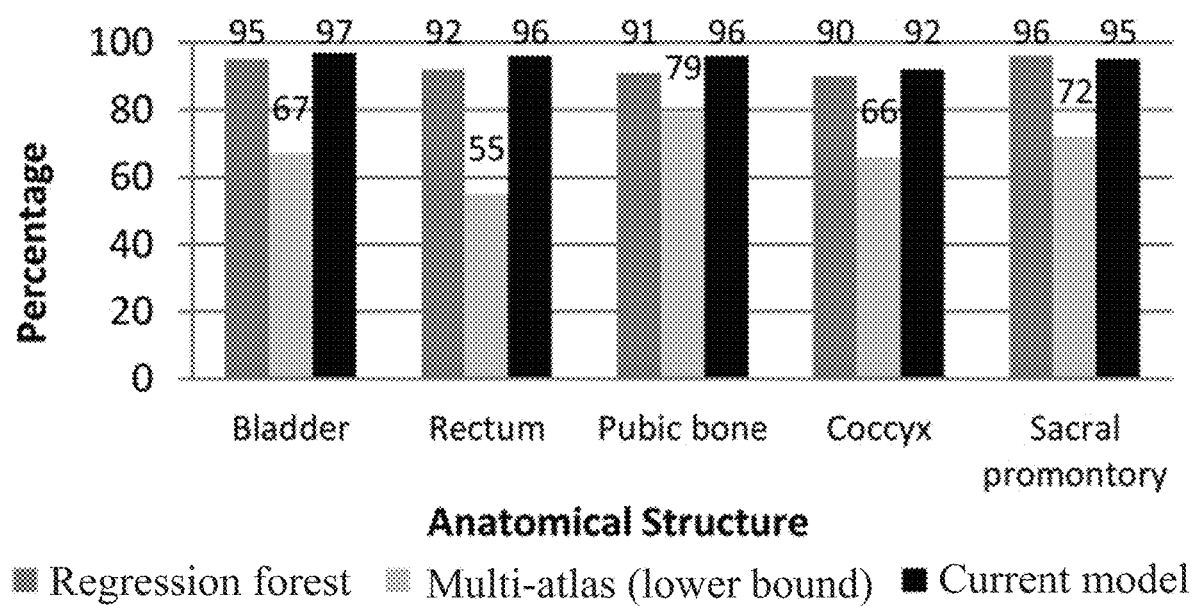
FIG. 10A depicts percentage of correctly detected cases by the current bone localization model compared to conventional localization models for a threshold of DSI 0.65.
Figure 10B:
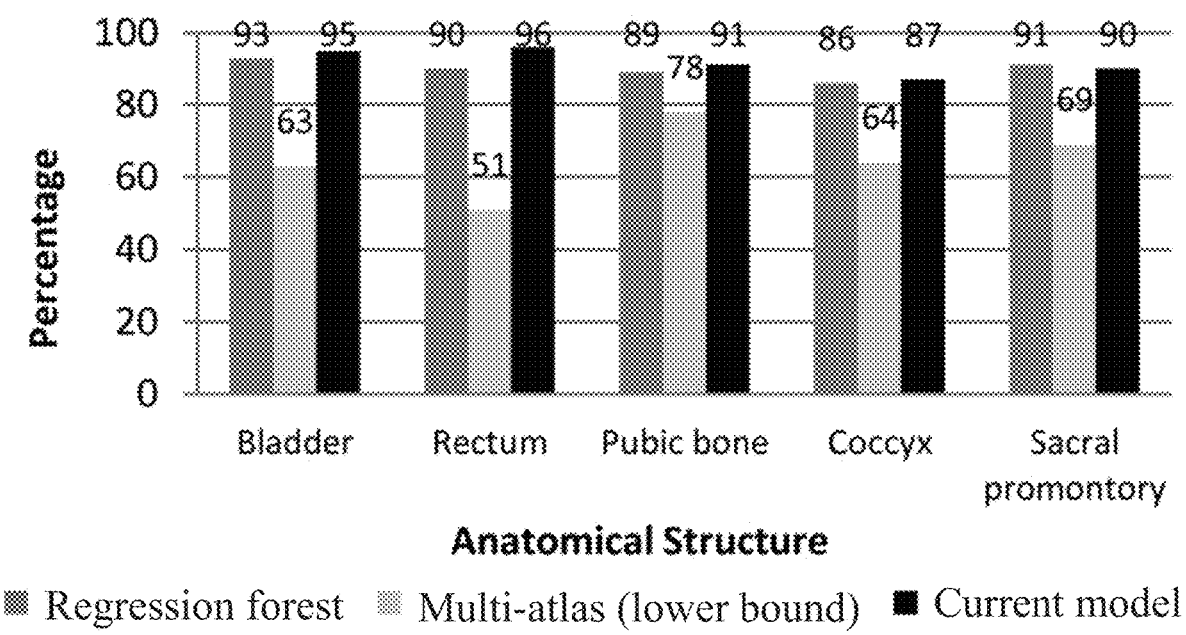
FIG. 10B depicts percentage of correctly detected cases by the current bone localization model compared to conventional localization models for a threshold of 0.75.
Figure 10C:
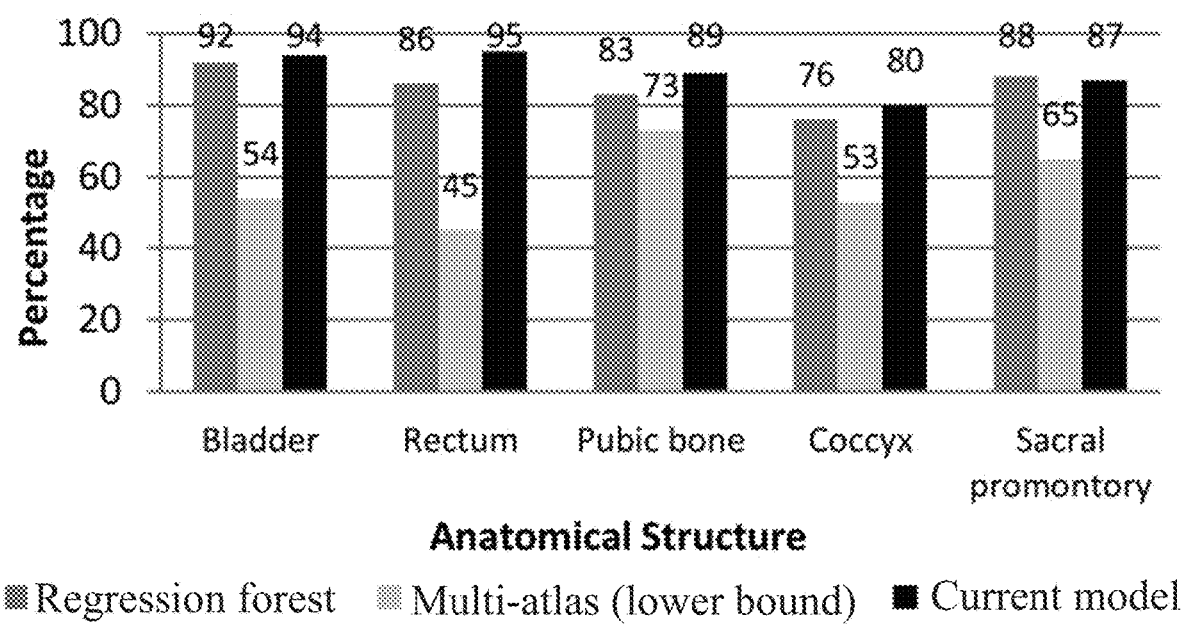
FIG. 10C depicts percentage of correctly detected cases by the current bone localization model compared to conventional localization models for a threshold of 0.90.

The current localization model was also compared with conventional methods based on DSI. FIGS. 10A-10C provide the average percentage of correctly detected cases at different thresholds for DSI. It can be observed that even at very high thresholds for DSI (DSI>0.90), the current methodology can correctly detect the pubic bone, sacral promontory, and coccyx in 89%, 87%, and 80%, respectively. Once the overlapping percentage between two regions is decreased to 0.75, the current method correctly detected the pubic bone, sacral promontory, and coccyx in 91%, 90%, and 87%, respectively. Compared to conventional methods, the current localization method achieved the highest average percentage of detection over all the thresholds of DSI and for all the anatomical structures except for the sacral promontory, where it performed very similar to the regression forest.

In terms of computational time, the current model provides the regions faster than the regression forest and multiatlas-based model. The current model identifies the location of the bone structures in 1.3 s compared with 2.1 s by the regression forest, and 13.2 s by the multiatlas-based model, thus improving the function of the underlying computer itself. Regarding the training time, the current model takes 5.6 s compared with 28.0 s for the regression forest, also evidencing improvement of computer function. The multiatlas-based model does not require a training process but overall, the computational time is higher and accuracy is much lower than the current localization model. For the regression forest, the time for model building will increase significantly whenever new data are included into the training dataset as it requires exhaustive search of parameters for the node optimization process to find the forest size and tree depth.

Figure 11A:
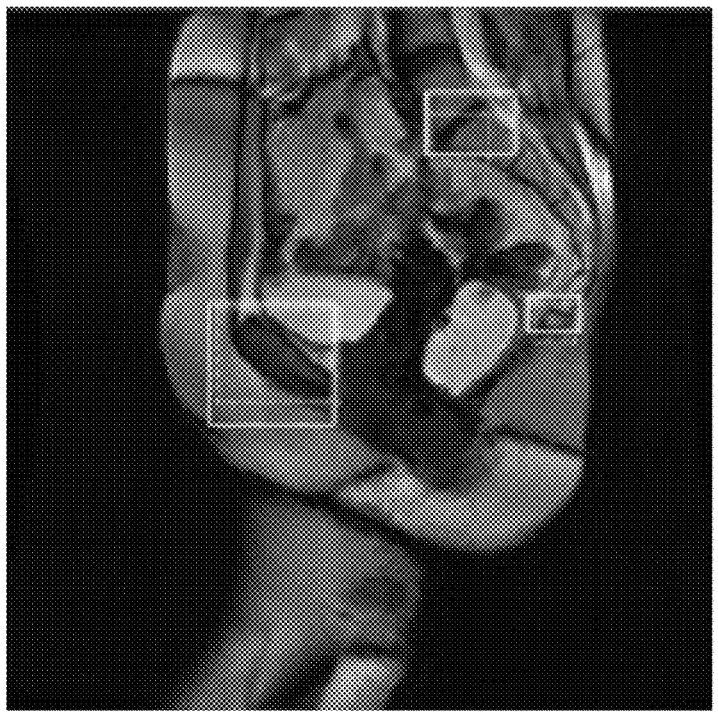
FIG. 11A depicts regions identified by the current location model with their corresponding ground truth regions.
Figure 11B:
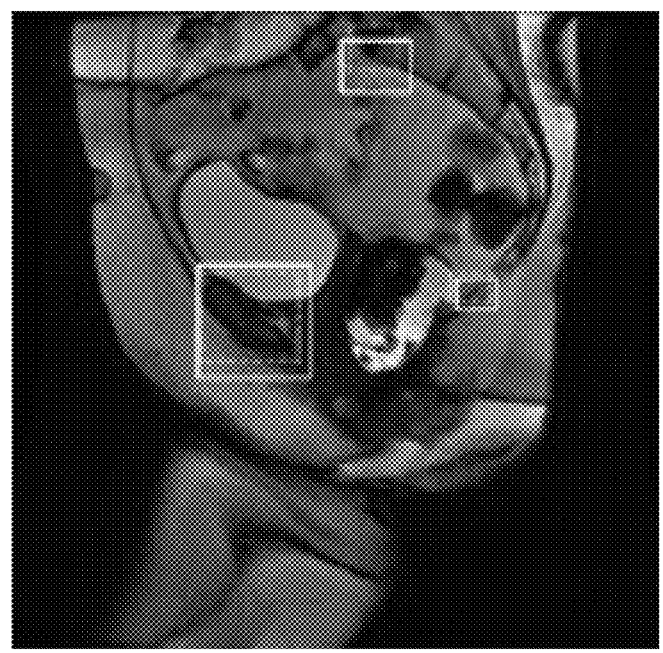
FIG. 11B depicts regions identified by the current location model with their corresponding ground truth regions.

FIGS. 11A-11B show sample localization results of the current model compared to the ground truth regions of the pubic bone, sacral promontory, and coccyx. The regions shown with solid lines correspond to the regions found by the current method, while regions with dashed lines indicate the ground truth regions.

III. Discussion

A model was presented herein that integrates local and global information to locate the bounding boxes of bone structures on MRI using SVM and nonlinear regression. The main contribution of this methodology is a new parameterization paradigm through a non-linear regression approach for the multiple-bone localization problem on MRI. The location of the pubic bone is determined based on the relative location with respect to the pelvic organs and using an SVM-based classification with Haar-like and texture features. The coccyx and sacral promontory are located using a non-linear regression model. Results demonstrate that the current methodology can accurately and consistently find the locations of the pubic bone, coccyx, and sacral promontory on MRI. Moreover, it achieves higher localization accuracy compared to conventional localization methods.

Center error between automatically and manually identified pubic bone regions has been found to be lower than those for coccyx and sacral promontory. The reason is that local information of the pubic bone was incorporated into the localization process along with the global information. As was seen in Table VI, the center error is highest for the coccyx since currently the manual identification of the coccyx region is difficult and subjective, resulting in lower localization accuracy for this region.

The advantages of the current method are that is robust and fully automated. It uses human anatomic information, such as relative positions of the anatomical structures to find the bone structures. The current localization method has been integrated with the segmentation and reference point identification techniques presented in the current inventors' previous work [7, 48] to fully automate the extraction of pelvic floor measurements for POP diagnosis.

In conclusion, a model using SVM based classification and non-linear regression model with global and local information was presented to automatically localize multiple pelvic bone structures on MRI. The main contribution of this approach is a new parameterization through non-linear regression approach for the multiple-bone localization problem on MRI. The model uses the location of pelvic organs to approximate the relative location of the pelvic bones. The best pubic bone region is selected using a SVM classifier based on texture and Haar-like features. Then, a non-linear regression model was built to establish the association between the locations of the bladder, rectum, and pubic bone with respect to the location of the sacral promontory and coccyx. Results demonstrated that the current method can accurately find the location of the bone structures on each image consistently. The current automated bone localization methodology can be used to automatically identify regions of interest to extract image based predictors for pelvic floor measurements. This can be expected to improve and facilitate the diagnosis of POP.

REFERENCES

[1] P. Dallenbach, Kaelin-Gambirasio, I., Jacob, S., Dubuisson, J. B., Boulvain, M., "Incidence rate and risk factors for vaginal vault prolapse repair after hysterectomy," Int Urogynecol J, vol. 19, pp. 1623-1629, 2008.

[2] R. C. Bump, Mattiasson, A., Bo, K., Brubaker, L. P., DeLancey, J. O. L., Klarskov, P., Shull, B. L., Smith, A. R. B., "The Standardization of Terminology of Female Pelvic Organ Prolapse and Pelvic Floor Dysfunction," Am J Obstet Gynecol, vol. 175, pp. 10-17, 1996.

[3] A. Fayyad, Hill, S., Gurung, V., Prashar, S., Smith, A., "How accurate is symptomatic and clinical evaluation of prolapse prior to surgical repair?." Int Urogynecol J, vol. 18, pp. 1179-1183, 2007.

[4] D. Altman, Lopez, A., Kierkegaard, J., Zetterstrom, J., Falconer, C., Pollack, J., Mellgren, A., "Assessment of Posterior Vaginal Wall Prolapse: Comparison of Physical Findings to Cystodefecoperitoneography," Int Urogynecol J Pelvic Floor Dysfunct, vol. 16, pp. 96-103, 2005.

[5] A. G. Groenendijk, vander-Hulst, V. P., Birnie, E., Bonsel, G. J., "Correlation between posterior vaginal wall defects assessed by clinical examination and by defecography," Int. Urogynecol J. vol. 19, pp. 1291-1297, 2008.

[6] M. Colaiacomo, C, Masselli, G., Polettini, E., Lanciotti, S., Casciani, E., Bertini, L., Gualdi, G., "Dynamic MR imaging of the pelvic floor: a pictorial review," Radiographics, p. e35, 2009.

[7] S. Onal, Lai-Yuen, S., Bao, P., Weitzenfeld, A., Hart, S., "Image based measurements for evaluation of pelvic organ prolapse," Journal of Biomedical Science and Engineering, vol. 6, pp. 45-55, 2013.

[8] S. R. Broekhuis, Futterer, J. J., Barentsz, J. O., Vierhout, M. E., "A systematic review of clinical studies on dynamic magnetic resonance imaging of pelvic organ prolapse: the use of reference lines and anatomical landmarks," Int Urogynecol J Pelvic Floor Dysfunct, vol. 20, pp. 721-729, 2009.

[9] M. M. Lakeman, Zijta, F. M., Peringa, J., Nederveen, A. J., Stoker, J., Roovers, J. P., "Dynamic magnetic resonance imaging to quantify pelvic organ prolapse: reliability of assessment and correlation with clinical findings and pelvic floor symptoms," Int. Urogynecol J., vol. 23, pp. 1547-1554, 2012.

[10] J. G. Tamez-Pena, Totterman, S., Parker, K. J., "Unsupervised statistical segmentation of multispectral volumetric MR images," 1999, pp. 300-311

[11] R. Adams, Bischof, L., "Seeded region growing," IEEE Trans. Pattern Anal. Machine Intell, vol. 16, pp. 641-647, 1994.

[12] J. Fripp, Crozier, S., Warfield, S. K., Ourselin, S., "Automatic segmentation of the bone and extraction of the bone-cartilage interface from magnetic resonance images of the knee," Phys. Med. Biol., vol. 52, pp. 1617-1631, 2007.

[13] M. H. Brem, Brem, M. H., Lang, P. K., Neumann, G., Schlechtweg, P. M., Schneider, E., Jackson, R., Yu, J., Eaton, C. B., Hennig, F. F., Yoshioka, H., Pappas, G., Duryea, J., "Magnetic resonance image segmentation using semi-automated software for quantification of knee articular cartilage—initial evaluation of a technique for paired scans," Skeletal Radiology vol. 28, pp. 505-511, 2008.
[14] T. F. Chan, Vese, L. A., "Active Contours Without Edges," IEEE Transaction on Image Processing, vol. 10, pp. 266-277, 2001.
[15] C. Li, "Distance Regularized Level Set Evolution and Its Application to Image Segmentation," IEEE Transactions on Image Processing, vol. 19, pp. 3243-3254, 2010.
[16] J. Folkesson, Dam, E. B., Olsen, O. F., Pettersen, P. C., Christiansen, C., "Segmenting articular cartilage automatically using a voxel classification approach," IEEE Transactions on Medical Imaging vol. 26, pp. 106-115, 2007.
[17] H. Shim, Chang, S., Tao, C., Wang, J. H., Kwoh, C. K., Bae, K. T., "Knee cartilage: Efficient and reproducible segmentation on highspatial-resolution MR images with the semiautomated graph-cut method," Radiology, vol. 251, pp. 548-556, 2009.
[18] L. Lorigo, "Segmentation of Bone in Clinical Knee MRI Using Based Geodesic Active Contours," presented at the MICCAI, 1998.
[19] J. Schmid, Magnenat-Thalmann, N., "MRI bone segmentation using deformable models and shape priors," Med. Image Comput, pp. 119-126, 2008.
[20] J. Carballido-Gamio, Belongie, S., Majumdar, S., "Normalized cuts in 3-D for spinal MRI segmentation," IEEE Trans. Med. Img., vol. 23, pp. 36-44, 2004.
[21] L. Liu, Raber, D., Nopachai, D., Commean, P., Sinacore, P., Prior, F., Pless, R., Ju, T., "Interactive separation of segmented bones in ct volumes using graph cut." presented at the MICCAI, ser. LNCS, 2008.
[22] Y. Boykov, Kolmogorov, V., "An experimental comparison of min-cut/maxflow algorithms for energy minimization in vision," IEEE Trans. Pattern Anal. Mach. Intell, vol. 26, pp. 1124-1137, 2004.
[23] Y. Y. Boykov, "Interactive graph cuts for optimal boundary & region segmentation of objects in N-D images" in Computer Vision, 2001. ICCV 2001. Proceedings. Eighth IEEE International Conference on, 2001, pp. 105-112.
[24] Y. Yin, Zhang, X., Sonka, M., "Optimal multi-object multi-surface graph search segmentation: Full-joint cartilage delineation in 3d," Proceedings of the Medical Image Understanding and Analysis, S. McKenna and J. Hoey, Eds, pp. 104-108, 2008.
[25] P. Bourgeat, Fripp, J., Stanwell, P., Ramadan, S., Ourselin, S., "MR image segmentation of the knee bone using phase information," Med. Image Anal., vol. 11, pp. 325-335, 2007.
[26] B. van Ginneken, Stegmann, M., Loog, M., "Segmentation of anatomical structures in chest radiographs using supervised methods: A comparative study on a public database", Medical Image Analysis vol. 10, pp. 19-40, 2006.
[27] S. Onal, Lai-Yuen, S., Hart, S., Bao, P., Weitzenfeld, A., "MRI-based Semi-Automatic Pelvimetry Measurement for Pelvic Organ Prolapse Diagnosis," in ISSPA 2012, Montreal, Quebec, Canada, 2012.
[28] R. M. Haralick, Shapiro, L. G., "Survey of image segmentation techniques," Computer Vision Graphics Image Process, vol. 29, pp. 100-132, 1985.
[29] S. M. Weiss, Predictive Data Mining: A Practical Guide. San Francisco, Ca: Morgan Kaufmann, 1998.
[30] C. W. Chen, Luo, J., Parker, K. J., "Image segmentation via adaptive K-mean clustering and knowledge based morphological operations with biomedical applications" IEEE Transactions on Image Processing, vol. 7, pp. 1673-1683 1998.
[31] M. Steinbach, Karypis, G., Kumar, V. (2000). A Comparison of Document Clustering Techniques. (M. Grobelnik, D. Mladenic, & N. Milic-Frayling, Eds.) KDD workshop on text mining, 400(X), 1-2. IEEE.
[32] C. Schmid, Mohr, R., Bauckhage, C., "Evaluation of interest point detectors," International Journal of Computer Vision, vol. 37, pp. 151-172, 2000.
[33] J. Cui, Sahiner, B., Chan, H. P., "A new automated method for the segmentation and characterization of breast masses on ultrasound images," Med. Phys., vol. 36, pp. 1553-1565, 2009.
[34] S. Maghsoodloo, "Strengths and limitations of taguchi's contributions to quality, manufacturing, and process engineering," Manufacturing systems, vol. 23, pp. 73-126, 2004.
[35] U. Kurkure, Avila-Montes, O. C., Kakadiaris, I. A., "Automated segmentation of thoracic aorta in non-contrast CT images," presented at the IEEE Intl. Symp. Biomedical Im., 2008.
[36] B. Van Ginneken, Baggerman, W., van Rikxoort, E. M., "Robust segmentation and anatomical labeling of the airway tree from thoracic CT scans," presented at the MICCAI, 2008.
[37] H. A. Vrooman, Cocosco, C. A., "kNN-based Multispectral MRI Brain Tissue Classification: Manual Training versus Automated Atlas-based Training," in Proceedings of the SPIE Medical Imaging, California, USA, 2006.
[38] M. Fenchel, Thesen, S., Schilling, A., "Automatic labeling of anatomical structures in MR fastview images using a statistical atlas," MICCAI, 2008.
[39] A. Shimizu, Ohno, R., Ikegami, T., Kobatake, H., "Multi-organ segmentation in three-dimensional abdominal CT images," Int. J CARS, vol. 1, 2006.
[40] X. Han, Hoogeman, M. S., Levendag, P. C., Hibbard, L. S., Teguh, D. N., Voet, P., Cowen, A. C., Wolf, T. K., "Atlas-based auto-segmentation of head and neck CT images," presented at the MICCAI, New York, N.Y., USA, 2008.
[41] M. Freiman, Edrei, Y., Shmidmayer, Y., Gross, E., Joskowicz, L., Abramovitch, R., "Classification of liver metastases using MRI images: A machine learning approach," presented at the MICCAI, 2008.
[42] M. Prasad, Sowmya, A., "Multi-level classification of emphysema in HRCT lung images using delegated classifiers," presented at the MICCAI, 2008.
[43] Y. Zheng, Barbu, A., Georgescu, B., Scheuering, M., Comaniciu, D., "Four-chamber heart modeling and automatic segmentation for 3-D cardiac CT volumes using marginal space learning and steerable features," IEEE Transactions on Medical Imaging vol. 27, pp. 1668-1681, 2008.
[44] Y. Zheng, Comaniciu, D., "Marginal Space Learning for Efficient Detection of 2D/3D Anatomical Structures in Medical Images," presented at the Information Processing in Medical Imaging, Williamsburg, Va., USA, 2009.
[45] S. K. Zhou, Zhou, J., Comaniciu, D., "A boosting regression approach to medical anatomy detection," presented at the IEEE Conference on Computer Vision and Pattern Recognition, 2007.
[46] A. Criminisi, Shotton, J., Robertson, D., Konukoglu, E., "Regression Forests for Efficient Anatomy Detection and Localization in CT Studies," presented at the Medical Image Computing Computer-Assisted Intervention Conf., Beijing, China, 2010.

[47] R. Cuingnet, R. Prevost, D. Lesage, L. Cohen, B. Mory, and R. Ardon. "Automatic Detection and Segmentation of Kidneys in 3D CT Images Using Random Forests," in Medical Image Computing and Computer-Assisted Intervention—MICCAI 2012. vol. 7512, ed, 2012, pp. 66-74.

[48] S. Onal, Lai-Yuen, S., Bao, P., Weitzenfeld, A., Hart, S., "MRI based Segmentation of Pubic Bone for Evaluation of Pelvic Organ Prolapse," IEEE Journal of Biomedical and Health Informatics, vol. 18, no, 4, pp. 1370-1378, July 2014.

[49] K. Polat, Gunes, S., "Breast cancer diagnosis using least square support vector machine," Digital Signal Processing, vol. 17, pp. 694-701, 2007.

[50] M. F. Akay, "Support vector machines combined with feature selection for breast cancer" Expert Systems with Applications, Elsevier, vol. 36, pp. 3240-3247, 2009.

[51] Mouritsen L, Larsen, J. P. Symptoms, bother and POPQ in women referred with pelvic organ prolapse. Int Urogynecol J Pelvic Floor Dysfunct. 2003, 14:122-7.

[52] Goh V, Halligan, S., Kaplan, G., Healy, J. C., Bartram, C. I. Dynamic MR imaging of the pelvic floor in asymptomatic subjects. AJR Am J Roentgenol. 2000, 174:661-6. PubMed Central PMCID: PMC10701605

[53] Healy J. C. H S, Reznek R. H. Dynamic MR imaging compared with evacuation proctography when evaluating anorectal configuration and pelvic floor movement. AJR Am J Roentgenol 1997; 169:775-9. PubMed Central PMCID: PMC9275895

[54] Lienemann A. A C, Baron A., Kohn P., Reiser M. Dynamic MR colpocystorectography assessing pelvic floor descent. Eur Radiol 1997; 7:1309-17. PubMed Central PMCID: PMC9377520

[55] Onal S., Lai-Yuen, S., Bao, P., Weitzenfeld, A., Greene, K., Kedar, R., Stuart, H. Assessment of a Semi-Automated Pelvic Floor Measurement Model for the Evaluation of Pelvic Organ Prolapse on MRI. International Urogynecology Journal 2014. doi: 10.1007/s00192-013-2287-4.

[56] Ubeyli E D. Implementing automated diagnostic systems for breast cancer detection. Expert Systems with Applications, Elsevier. 2007; 33(4): 1054-62.

[57] Lienemann A, Sprenger, D., Janssen, U., Grosch, E., Pellengahr, C., Anthuber, C. Assessment of pelvic organ descent by use of functional cine-MRI: which reference line should be used?. Neurourol Urodyn 2004; 23:33-7.

[58] Gousse A E, Barbaric, Z. L., Safir, M. H., Madjar, S., Marumoto, A. K., Raz, S. Dynamic half Fourier acquisition, single shot turbo spin-echo magnetic resonance imaging for evaluating the female pelvis. J Urol. 2000; 164:1606-13.

[59] Kelvin F. M. HDS, Maglinte D. D., Patten B. J., Benson J. T. Female pelvic organ prolapse: diagnostic contribution of dynamic cystoproctography and comparison with physical examination. AJR Am J Roentgenol 1999; 173: 31-7.

[60] Fauconnier A, Zareski, E., Abichedid, J., Bader, G., Falissard, B., Fritel, X. Dynamic magnetic resonance imaging for grading pelvic organ prolapse according to the international continence society classification: Which line should be used?. Neurourol Urodyn 2007; 27:191-7.

[61] Pannu K. H., Scatarige, C., J., Eng, J. MRI Diagnosis of Pelvic Organ Prolapse Compared with Clinical Examination. Academic Radiology. 2011; 18(10):1245-51. PubMed Central PMCID: PMC21795069.

[62] Cortes E, Reid, W., M., N., Singh, K., Berger, L. Clinical Examination and Dynamic Magnetic Resonance Imaging in Vaginal Vault Prolapse. Obstetrics & Gynecology. 2004; 103:41-6.

[63] Robinson C J, Swift, S., Johnson, D. D., Almeida, J. S. Prediction of pelvic organ prolapse using an artificial neural network. American Journal of Obstetrics and Gynecology. 2008:193.e1-.e6.

[64] Ismail S I M F et al., "Unilateral coronal diameters of the levator hiatus: baseline data for the automated detection of avulsion of the levator ani muscle", Journal; Article; (JOURNAL ARTICLE) E-ISSN:1469-0705 Journal Code:9108340 England: United Kingdom 36(4): 375-378 (2010)

[65] Christopher J. Robinson et al., "Prediction of pelvic organ prolapse using an artificial neural network", American Journal of Obstetrics and Gynecology, ISSN 0002-9378, 199(2): 193.e1-193.e6 (August 2008)

[66] Speksnijder L et al., "Agreement and reliability of pelvic floor measurements during contraction using three-dimensional pelvic floor ultrasound and virtual reality", Ultrasound in obstetrics & gynecology: the official journal of the International Society of Ultrasound in Obstetrics and Gynecology, E-ISSN:1469-0705 Journal Code: 9108340 England: United Kingdom, 40(1): Pages 87-92 (2012)

[67] Rahim M, Bellemare M E et al., "Automatic estimation of pelvic organ anatomical references", IEEE Eng Med Biol Soc. 2011, doi: 10.1109/IEMBS.2011.6091269, 2011: 5124-5127

[68] David Pasquier et al., "Automatic Segmentation of Pelvic Structures From Magnetic Resonance Images for Prostate Cancer Radiotherapy", International Journal of Radiation Oncology*Biology*Physics, ISSN 0360-3016, 68(2): 592-600 (1 Jun. 2007)

[69] P. Viola and J. J. Michael, "Rapid object detection using a boosted cascade of simple features," in Proc. IEEE Comput. Soc. Conf. Comput. Vis. Pattern Recog., 2001, pp. I-511-I-518.

[70] T. Rohlfing, R. Brandt, R. Menzel, and C. R. Maurer Jr., "Evaluation of atlas selection strategies for atlas-based image segmentation with application to confocal microscopy images of bee brains," Neuroimage, vol. 21, no. 4, pp. 1428-1442, 2004.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

Hardware and Software Infrastructure Examples

The present invention may be embodied on various computing platforms that perform actions responsive to software-based instructions and most particularly on touch-screen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C #, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

Glossary of Claim Terms

Candidate bounding boxes: This term is used herein to refer to a virtual enclosure that surrounds a keypoint or set of keypoints, defining a particular set of features based on certain intensity and location constraints.

Classifier: This term is used herein to refer to a learning model that analyzes images and data used for classification of the underlying image/data. The classification is then used to predict or diagnose POP based on said analysis.

Clinical information: This term is used herein to refer to any data or analysis that can be used to train the system to identify particular keypoints (e.g., by setting the intensity and location constraints), or to otherwise aid in how a particular patient's MRI image compares to previous images, for example including, but not limited to, global information, the patient's demographic information, and mean shape information of features.

Clustered cartilage: This term is used herein to refer to a leak that can be removed to provide higher clarity for identifying and visualizing the pubic bone.

Feature: This term is used herein to refer to an anatomical or image-based quality/characteristic found in an MRI image, Keypoint: This term is used herein to refer to a point on the input MRI image that satisfies certain intensity and location constraints based on clinical information, such as mean intensity/shape of a particular structure of interest. Based on the keypoints, candidate bounding boxes can be determined.

Leak detection: This term is used herein to refer to identifying and correcting leaks in the MRI image, where leaks refer to the similar-intensity characteristics of bone and soft tissue, where soft tissue regions may be occasionally included into the bone region. This typically occurs when the pubic bone and background regions (soft tissue, cartilage and fat regions) become joined together due to the lack of strong edges between them.

Low level contrast intensity: This term is used herein to refer to lesser differences in lightness, brightness, and/or hue in an image, such that these lesser differences can lead to difficulties in distinguishing particular aspects/structures within the image.

Reference point: This term is used herein to refer to a basis, standard, or point that can describe the location of another point, or can otherwise form the basis of assessing locations of other structures.

Substantially around: This term is used herein to refer to the bounding boxes completely or partially enclosing the pelvic structures.

Training data set: This term is used herein to refer to a collection of data that is used to provide a classifier or other component/system a standard to which the patient's MRI image can be compared or otherwise relativized in order to predict or diagnose POP.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A tangible non-transitory computer readable storage media having computer-executable instructions for a computer processor to perform a method for predicting or diagnosing pelvic organ prolapse, the instructions comprising:

receiving an image of a patient from a magnetic resonance imaging (MRI) procedure performed around a pelvic area of the patient;

automatically identifying a location of a bladder and a rectum of the patient within the MRI image based on their intensity values displayed on the MRI image;

automatically identifying a pubic bone of the patient within said MRI image, wherein the step of identifying the pubic bone comprises:

automatically extracting and identifying keypoints on the pubic bone and on a pelvic floor on the MRI image based on a spatial relationship between the pelvic organs and pubic bone structures, automatically generating candidate bounding boxes substantially around the pubic bone structures, automatically extracting features within the bounding boxes, and classifying the candidate bounding boxes using an automated classifier having a learning algorithm that analyzes data used for classification analysis;

wherein the classifier is constructed based on a training data set using a support vector machine (SVM) trained using a radial basis function kernel providing for non-linear decision surface;

wherein the SVM-based classifier classifies each candidate bounding box using Haar-like and texture features, each candidate bounding box being classified as an enclosed pubic bone region and a partially enclosed pubic bone region;

automatically identifying a coccyx and a sacral promontory of the patient within the MRI image, wherein the step of identifying the coccyx and the sacral promontory comprises:

wherein using locations of the bladder, the rectum, and the pubic bone structures to localize the coccyx and the sacral promontory via a non-linear regression; and automatically linking the extracted features of the pubic bone structures and the localized coccyx and sacral promontory with clinical information to predict or diagnose pelvic organ prolapse.

2. The tangible non-transitory computer readable storage media of claim 1, wherein the keypoints on the pelvic floor are corner points on the MRI image, such that the corner points can be extracted using a corner point detector.

3. The tangible non-transitory computer readable storage media of claim 1, wherein the bounding boxes are centered at the keypoints and a size of each bounding box is based on a mean shape of pubic bone as determined by the clinical information.

4. The tangible non-transitory computer readable storage media of claim 1, wherein when at least one of the keypoints becomes positioned near a boundary of a corresponding bounding box which thus does not completely enclose an underlying pubic bone structure, the bounding boxes that do completely enclose underlying pubic bone structures are identified by analyzing each bounding box based on Haar-like and texture features.

5. The tangible non-transitory computer readable storage media of claim 1, wherein the step of extracting features within the bounding boxes is performed using 2D box and texture features in order to enhance features of the pubic bone structures.

6. The tangible non-transitory computer readable storage media of claim 1, further comprising eliminating any keypoints outside of a vicinity of the bladder and the rectum via spatial filtering between the step of extracting the keypoints and the step of identifying the keypoints.

7. The tangible non-transitory computer readable storage media of claim 1, wherein the training data set includes training features found to be significant using independent significance feature selection and selected using sequential forward selection by k-fold cross-validation.

8. The tangible non-transitory computer readable storage media of claim 1, wherein the non-linear regression is trained through parameterizing a location of pelvic floor structures with respect to the bladder, the rectum and the pubic bone structures.

9. The tangible non-transitory computer readable storage media of claim 1, wherein the step of identifying the coccyx and the sacral promontory further comprises determining centroids of the sacral promontory and the coccyx and generating additional bounding boxes substantially around the coccyx and the sacral promontory, where the additional bounding boxes are centered at the centroids.

10. The tangible non-transitory computer readable storage media of claim 1, wherein the keypoints on said pubic bone are identified using morphological skeleton operation and the keypoints on a vertebra of the patient are identified using intersecting point detection.

11. The tangible non-transitory computer readable storage media of claim 1, further comprising segmenting the pubic bone and corresponding cartilage to identify the keypoints on said pubic bone.

12. The tangible non-transitory computer readable storage media of claim 1, wherein the extracted features include gray level features, such that texture features can be extracted using gray level co-occurrence matrix.

13. The tangible non-transitory computer readable storage media of claim 1, wherein the keypoints are further based on angles including an angle between a diagonal conjugate line and a pubococcygeal line for posterior prolapse and an angle between an obstetric conjugate line and a mid-pubic line for anterior prolapse.

14. The tangible non-transitory computer readable storage media of claim 13, wherein the keypoints are further based on reference lines including a true conjugate line, the obstetric conjugate line, and the diagonal conjugate line.

15. The tangible non-transitory computer readable storage media of claim 1, further comprising implementing a relaxation stage to smooth an output of said classifier to reduce any errors produced by the classifier.

16. The tangible non-transitory computer readable storage media of claim 15, wherein the relaxation stage includes a first phase morphological operation that removes misclassified background, a filling operation to fill small gaps, and a thinning operation to remove regions smaller than about 100 pixels.

17. The tangible non-transitory computer readable storage media of claim 1, wherein the step of identifying the bladder and the rectum includes using a bisecting k-means clustering and morphological opening operations to identify pelvic organs, including the bladder and the rectum.

18. The tangible non-transitory computer readable storage media of claim 17, wherein the value of k is four (4) in the k-means clustering representing bone region, cartilage region, soft tissue, and organ region, and background region.

19. The tangible non-transitory computer readable storage media of claim 18, further comprising performing leak detection to remove clustered cartilage during classification of the candidate bounding boxes.

20. The tangible non-transitory computer readable storage media of claim 18, wherein the k-means clustering identifies the cartilage region the texture-based classification identifies the bone region, wherein the cartilage region and the bone region are combined to find reference points for assessing the pelvic organ prolapse.

21. The tangible non-transitory computer readable storage media of claim 17, wherein the step of identifying the bladder and the rectum includes reducing noise and adjusting contrast in the MRI image to normalize the MRI image.

22. The tangible non-transitory computer readable storage media of claim 21, wherein the noise is reduced by applying a convolution operation onto the MRI image with a smoothing kernel.

* * * * *